US010301637B2

(12) United States Patent
Clasen et al.

(10) Patent No.: US 10,301,637 B2
(45) Date of Patent: May 28, 2019

(54) POTATOES WITH REDUCED GRANULE-BOUND STARCH SYNTHASE

(71) Applicant: CELLECTIS, Paris (FR)

(72) Inventors: Benjamin Clasen, South St Paul, MN (US); Daniel F. Voytas, Falcon Heights, MN (US); Feng Zhang, Plymouth, MN (US)

(73) Assignee: CELLECTIS, Paris (FR)

( * ) Notice: Subject to any disclaimer, the term of this patent is extended or adjusted under 35 U.S.C. 154(b) by 0 days.

(21) Appl. No.: 14/744,386

(22) Filed: Jun. 19, 2015

(65) Prior Publication Data

US 2015/0368659 A1 Dec. 24, 2015

Related U.S. Application Data

(60) Provisional application No. 62/014,808, filed on Jun. 20, 2014.

(51) Int. Cl.
*C12N 15/82* (2006.01)
*C08B 30/04* (2006.01)

(52) U.S. Cl.
CPC ........ *C12N 15/8245* (2013.01); *C08B 30/048* (2013.01); *C12N 15/8213* (2013.01)

(58) Field of Classification Search
None
See application file for complete search history.

(56) References Cited

U.S. PATENT DOCUMENTS

| | | | |
|---|---|---|---|
| 4,179,337 A | 12/1979 | Davis et al. | |
| 4,683,195 A | 7/1987 | Mullis et al. | |
| 4,761,373 A | 8/1988 | Anderson et al. | |
| 4,769,061 A | 9/1988 | Comai | |
| 4,810,648 A | 3/1989 | Stalker | |
| 4,940,835 A | 7/1990 | Shah et al. | |
| 4,959,317 A | 9/1990 | Sauer | |
| 4,975,374 A | 12/1990 | Goodman et al. | |
| 5,006,333 A | 4/1991 | Saifer et al. | |
| 5,013,659 A | 5/1991 | Bedbrook et al. | |
| 5,162,602 A | 11/1992 | Somers et al. | |
| 5,204,253 A | 4/1993 | Sanford et al. | |
| 5,276,268 A | 1/1994 | Strauch et al. | |
| 5,356,802 A | 10/1994 | Chandrasegaran | |
| 5,436,150 A | 7/1995 | Chandrasegaran | |
| 5,487,994 A | 1/1996 | Chandrasegaran | |
| 5,501,967 A | 3/1996 | Offringa et al. | |
| 5,538,880 A | 7/1996 | Lundquist et al. | |
| 5,554,798 A | 9/1996 | Lundquist et al. | |
| 5,561,236 A | 10/1996 | Leemans et al. | |
| 5,591,616 A | 1/1997 | Hiei et al. | |
| 5,767,366 A | 6/1998 | Sathasivan et al. | |
| 5,792,640 A | 8/1998 | Chandrasegaran | |
| 5,879,903 A | 3/1999 | Strauch et al. | |
| 5,928,937 A | 7/1999 | Kakefuda et al. | |
| 6,084,155 A | 7/2000 | Volrath et al. | |
| 6,326,166 B1 | 12/2001 | Pomerantz et al. | |
| 6,329,571 B1 | 12/2001 | Hiei | |
| 6,368,227 B1 | 4/2002 | Olson | |
| 6,451,732 B1 | 9/2002 | Beckett et al. | |
| 6,451,735 B1 | 9/2002 | Ottaway et al. | |
| 6,784,338 B1* | 8/2004 | Hofvander | C12N 9/1051 435/101 |
| 6,824,978 B1 | 11/2004 | Cox, III et al. | |
| 6,933,113 B2 | 8/2005 | Case et al. | |
| 6,979,539 B2 | 12/2005 | Cox, III et al. | |
| 7,001,768 B2 | 2/2006 | Wolffe | |
| 7,013,219 B2 | 3/2006 | Case et al. | |
| 7,067,722 B2 | 6/2006 | Fillatti | |
| 7,070,934 B2 | 7/2006 | Cox, III et al. | |
| 7,163,824 B2 | 1/2007 | Cox, III et al. | |
| 7,189,691 B2 | 3/2007 | Hemenway | |
| 7,220,719 B2 | 5/2007 | Case et al. | |
| 7,262,054 B2 | 8/2007 | Jamieson et al. | |
| 7,273,923 B2 | 9/2007 | Jamieson et al. | |
| 7,285,416 B2 | 10/2007 | Choo et al. | |
| 7,361,635 B2 | 4/2008 | Miller et al. | |
| 7,521,241 B2 | 4/2009 | Choo et al. | |
| 7,842,489 B2 | 11/2010 | Arnould et al. | |
| 8,420,782 B2 | 4/2013 | Bonas et al. | |
| 8,440,431 B2 | 5/2013 | Voytas et al. | |
| 8,440,432 B2 | 5/2013 | Voytas et al. | |
| 8,450,471 B2 | 5/2013 | Voytas et al. | |
| 8,586,363 B2* | 11/2013 | Voytas | C12N 9/22 435/440 |
| 8,697,853 B2 | 4/2014 | Voytas et al. | |
| 9,035,129 B2 | 5/2015 | Bilyeu et al. | |

(Continued)

FOREIGN PATENT DOCUMENTS

| | | |
|---|---|---|
| EP | 0 242 246 | 10/1987 |
| EP | 2 206 723 | 7/2010 |

(Continued)

OTHER PUBLICATIONS

Hovenkamp-Hermelink et al 1987 Theor Appl Genet 75:217-221.*
Muth et al 2008 Plant Biotechnology Journal 6:576-584.*
U.S. Appl. No. 61/225,043, filed Jul. 13, 2009, Bonas et al.
"TAL effector nucleases," Nature Reprint Collection [online]. Oct. 2011, [retrieved Mar. 14, 2012]. Retrieved from the Internet: URL <http://www.nature.com/nbt/collections/talen/index.html>, 32 pages, Marshall (ed.).

(Continued)

*Primary Examiner* — Brent T Page

(74) *Attorney, Agent, or Firm* — Fish & Richardson P.C.

(57) ABSTRACT

Materials and methods for making plants (e.g., *Solanum* varieties) with decreased levels of amylose are provided herein. The methods can include making mutations in the gene encoding granule bound starch synthase (GBSS), where the mutations are induced using a rare-cutting endonuclease.

9 Claims, 8 Drawing Sheets

Specification includes a Sequence Listing.

(56) References Cited

U.S. PATENT DOCUMENTS

| | | | |
|---|---|---|---|
| 9,198,365 | B2 | 12/2015 | Bilyeu et al. |
| 2001/0016956 | A1 | 8/2001 | Ward et al. |
| 2005/0064474 | A1 | 3/2005 | Umov et al. |
| 2007/0141038 | A1 | 6/2007 | Choulika et al. |
| 2009/0060921 | A1 | 3/2009 | Dickey et al. |
| 2009/0133158 | A1 | 5/2009 | Lahaye et al. |
| 2009/0271881 | A1 | 10/2009 | Arnould et al. |
| 2009/0305402 | A1 | 12/2009 | Liljedahl et al. |
| 2010/0132069 | A1 | 5/2010 | Lahaye et al. |
| 2010/0154081 | A1 | 6/2010 | Weterings et al. |
| 2011/0041195 | A1 | 2/2011 | Doyon |
| 2011/0129898 | A1 | 6/2011 | Doyon et al. |
| 2011/0136895 | A1 | 6/2011 | Gregory et al. |
| 2011/0145940 | A1* | 6/2011 | Voytas ............ C12N 9/22 800/13 |
| 2011/0158957 | A1 | 6/2011 | Bonini et al. |
| 2011/0167521 | A1 | 7/2011 | DeKelver et al. |
| 2011/0201055 | A1 | 8/2011 | Doyon et al. |
| 2011/0201118 | A1 | 8/2011 | Yang et al. |
| 2011/0203012 | A1 | 8/2011 | Dotson et al. |
| 2011/0207221 | A1 | 8/2011 | Cost et al. |
| 2011/0239315 | A1 | 9/2011 | Bonas et al. |
| 2011/0247089 | A1 | 10/2011 | Doyon |
| 2011/0265198 | A1 | 10/2011 | Gregory et al. |
| 2011/0269234 | A1 | 11/2011 | Doyon et al. |
| 2011/0287545 | A1 | 11/2011 | Cost et al. |
| 2011/0301073 | A1 | 12/2011 | Gregory et al. |
| 2012/0110685 | A1 | 5/2012 | Bonas et al. |
| 2012/0122205 | A1 | 5/2012 | Bonas et al. |
| 2012/0178131 | A1 | 7/2012 | Voytas et al. |
| 2012/0178169 | A1 | 7/2012 | Voytas et al. |
| 2012/0214228 | A1 | 8/2012 | Voytas et al. |
| 2012/0246764 | A1 | 9/2012 | Hlubek et al. |
| 2012/0284877 | A1 | 11/2012 | Hlubek et al. |
| 2012/0324603 | A1 | 12/2012 | Hlubek et al. |
| 2013/0122581 | A1 | 5/2013 | Voytas et al. |
| 2014/0090116 | A1 | 3/2014 | Ainley et al. |

FOREIGN PATENT DOCUMENTS

| | | |
|---|---|---|
| EP | 2 392 208 | 12/2011 |
| EP | 2 562 260 | 2/2013 |
| WO | WO 92/11376 | 7/1992 |
| WO | WO 1994/18313 | 8/1994 |
| WO | WO 1995/09233 | 4/1995 |
| WO | WO 2003/033540 | 4/2003 |
| WO | WO 2004/067736 | 8/2004 |
| WO | WO 2007/060495 | 5/2007 |
| WO | WO 2008/141806 | 11/2008 |
| WO | WO 2009/095793 | 8/2009 |
| WO | WO 2010/079430 | 7/2010 |
| WO | WO 2010/091018 | 8/2010 |
| WO | WO 2010/145846 | 12/2010 |
| WO | WO 2011/005998 | 1/2011 |
| WO | WO 2011/017293 | 2/2011 |
| WO | WO 2011/019385 | 2/2011 |
| WO | WO 2011/072246 | 6/2011 |
| WO | WO 2011/100058 | 8/2011 |
| WO | WO 2011/117249 | 9/2011 |
| WO | WO 2011/146121 | 11/2011 |
| WO | WO 2011/154393 | 12/2011 |
| WO | WO 2012/106105 | 8/2012 |
| WO | WO 2013/050155 | 4/2013 |
| WO | WO 2014/039692 | 3/2014 |
| WO | WO 2014/039702 | 3/2014 |

OTHER PUBLICATIONS

Kuipers et al., "Formation and deposition of amylose in the potato tuber starch granule are affected by the reduction of granule-bound starch synthase gene expression," Plant Cell. Jan. 1994, 6(1):43-52.
Aiyer, "Amylases and their applications," African J. Biotech., Dec. 2005, 4(13):1525-1529.
Alam and Sittman, "Characterization of the cytotoxic effect of a chimeric restriction enzyme, H1°-FokI," Gene Ther Mol Biol, 10:147-160, 2006.
Alam, "Characterization of the cytotoxic effect of a novel chimeric restriction nuclease, H1°-FokI, in mouse fibroblast cells: Implications for chromatin mapping and gene therapy studies," Ph.D. Thesis, The University of Mississippi Medical Center, 223 pages, 2006.
Al-Saadi et al., "All five host-range variants of Xanthomonas citri carry one pthA homolog with 17.5 repeats that determines pathogenicity on citrus, but none determine host-range variation," Mol Plant Microbe Interact, 20(8): 934-943, 2007.
Amflora: Amylopectin Potato EH92-527-1 User Guide. BASF Plant Science Company GmbH. Mar. 2010.
Antony et al., "Rice xa13 recessive resistance to bacterial blight is defeated by induction of the disease susceptibility gene Os-11N3," Plant Cell, 22(11):3864-3876, 2010.
Antony, "Molecular basis of avrXa7 mediated virulence in bacterial blight of rice," [abstract of dissertation] Kansas State University, 99 pages, 2010.
Arimondo et al., "Exploring the cellular activity of camptothecin-triple-helix-forming oligonucleotide conjugates," Mol Cell Biol, 26:324-333, 2006.
Athinuwat et al., "Xanthomonas axonopodis pv. glycines soybean cultivar virulence specificity is determined by avrBs3 homolog avrXg1," Phytopathology, 99(8):996-1004, 2009.
Bai et al., "Xanthomonas oryzae pv. oryzae avirulence genes contribute differently and specifically to pathogen aggressiveness," Mol Plant Microbe Interact, 13(12):1322-1329, 2000.
Baker, "Gene-editing nucleases," Nature Methods, 2012, 9:23-26.
Ballvora et al., "Genetic mapping and functional analysis of the tomato Bs4 locus governing recognition of the Xanthomonas campestris pv. vesicatoria AvrBs4 protein," Mol Plant Microbe Interact, 14(5):629-638, 2001.
Beaujean et al., "*Agrobacterium*-mediated transformation of three economically important potato cultivars using sliced intermodal explants: an efficient protocol of transformation," J. Exp. Biol. 49:1589-1595, 1998.
Belahj et al., "Plant genome editing made easy: targeted mutagenesis in model and crop plants using the CRISPR/Cas system," Plant Methods, 9:39 (2013).
Beretta et al., "Tethering a type IB topoisomerase to a DNA site by enzyme fusion to a heterologous site-selective DNA-binding protein domain," Cancer Res, 59:3689-3697, 1999.
Bethke and Busse, "Validation of a simple, colorimetric, microplate assay using amplex red for the determination of glucose and sucrose in potato tubers and other vegetables," Am. J. Pot Res., 85:414-421 (2008).
Beuselinck et al., "An Assessment of Phenotype Selection for Linolenic Acid Using Genetic Markers," Crop Sci, 47:747-750 (2006).
Bhaskar et al., "Suppression of the vacuolar invertase gene prevents cold-induced sweetening in potato," Plant Physiol., 154(2):939-948 (Oct. 2010).
Bibikova et al., "Enhancing gene targeting with designed zinc finger nucleases," Science, 300(5620):764, 2003.
Bibikova et al., "Stimulation of homologous recombination through targeted cleavage by chimeric nucleases," Mol Cell Biol, 21(1): 289-297, 2001.
Bitinaite et al., "FokI dimerization is required for DNA cleavage," Proc Natl Acad Sci USA, 95:10570-10575, 1998.
Boch and Bonas. "Xanthomonas AvrBs3 family-type III effectors: discovery and function." Annu Rev Phytopathol, 48, 419-436, 2010.
Boch et al., "Breaking the code of DNA binding specificity of TAL-type III effectors," Science, 326:1509-1512, 2009.
Boch et al., "Molecular characterization of three AvrBs3-like effectors from the *Arabidopsis* pathogen Xanthomonas campestris pv. armoraciae," (abstract), XIV International Congress on Molecular Plant-Microbe Interactions, Quebec City, Canada, Jul. 19-23, 2009, 2 pages.
Bogdanove et al., "TAL effectors: Customizable Proteins for DNA Targeting," Science, 333: 1843-1846, 2011.

(56) References Cited

OTHER PUBLICATIONS

Bogdanove et al., "TAL effectors: finding plant genes for disease and defense," Curr Opin Plant Biol, 13:394-401, 2010.
Boller and He, "Innate immunity in plants: an arms race between pattern recognition receptors in plants and effectors in microbial pathogens," Science, 324:742-744, 2009.
Bonas et al., "Resistance in tomato to Xanthomonas campestris pv vesicatoria is determined by alleles of the pepper-specific avirulence gene avrBs3," Mol Gen Genet, 328: 261-269, 1993.
Bonas et al., "Genetic and structural characterization of the avirulence gene avrBs3 from Xanthomonas campestris pv. Vesicatoria," Mol Gen Genet, 218:127-136, 1989.
Bonas et al., "How the bacterial plant pathogen Xanthomonas campestris pv. vesicatoria conquers the host," Mol Plant Pathol, 1(1):73-76, 2000.
Bonas et al., "Resistance in tomato to Xanthomonas campestris pv vesicatoria is determined by alleles of the pepper-specific avirulence gene avrBs3," Mol Gen Genet, 238(1-2):261-269, 1993.
Bonas, "How Xanthomonas manipulates the plant cell," (abstract), XIV International Congress on Molecular Plant-Microbe Interactions, Quebec City, Canada, Jul. 19-23, 2009, 2 pages.
Borevitz et al., "Activation tagging identifies a conserved MYB regulator of phenylpropanoid biosynthesis," Plant Cell, 12:2383-2394, 2000.
Busk, "Regulatory elements in vivo in the promoter of the abscisic acid responsive gene rab 17 from maize," Plant J, 11:1285-1295, 1997.
Büttner and Bonas, "Getting across—bacterial type III effector proteins on their way to the plant cell," EMBO J, 2002, 21(20):5313-5322, 2002.
Büttner et al., "Functional analysis of HrpF, a putative type III translocon protein from Xanthomonas campestris pv. vesicatoria," J Bacteriol, 184(9):2389-2398, 2002.
Büttner et al., "HpaB from Xanthomonas campestris pv. vesicatoria acts as an exit control protein in type III-dependent protein secretion," Mol Microbiol, 54(3):755-768, 2004.
Büttner et al., "Targeting of two effector protein classes to the type III secretion system by a HpaC- and HpaB-dependent protein complex from Xanthomonas campestris pv. vesicatoria," Mol Microbiol, 59(2):513-527, 2006.
Canteros et al., "A gene from Xanthomonas campestris pv. vesicatoria that determines avirulence in tomato is related to avrBs3," Mol Plant Microbe Interact, 4(6):628-632, 1991.
Carlson et al., "Targeting DNA With Fingers and TALENs," Mol Ther Nucl Acids, 1:e3, doi:10.1038/mtna.2011.5, 4 pages, 2012.
Cathomen et al., "Zinc-finger nucleases: the next generation emerges," Mol Ther, 16(7):1200-1207, 2008.
Cavalier et al., "Disrupting two *Arabidopsis thaliana* xylosyltransferase genes results in plant deficient in xyloglucan, a major primary cell wall component," the Plant Cell, 20:1519-1537 (Jun. 2008).
Cermak et al., "Efficient design and assembly of custom TALEN and other TAL effector-based constructs for DNA targeting," Nucleic Acids Res, 39:e82 (2011).
Cermak et al., Poster and Abstract—"Engineered TAL effector nucleases: new tools for genome editing," Northwest Genome Engineering Consortium Workshop on Genome Engineering, 3 pages, 2010.
Chen et al., "Transfection and expression of plasmid DNA in plant cells by an arginine-rich intracellular delivery peptide without protoplast preparation," FEBS Lett, May 2007, 581(9): 1891-7.
Chevalier et al., "Design, activity, and structure of a highly specific artificial endonuclease," Mol Cell, 10(4):895-905, 2002.
Choo et al., "In vivo repression by a site-specific DNA-binding protein designed against an oncogenic sequences," Nature, 372(6507):642-645, 1994.
Choulika et al., "Induction of homologous recombination in mammalian chromosomes by using the I-SceI system of *Saccharomyces cerevisiae*," Mol Cell Biol, 15(4):1968-1973, 1995.
Christian et al., "Targeting DNA double-strand breaks with TAL effector nucleases," Genetics, 186:757-761 (2010).
Christian et al., Poster and Abstract—"Fusions of TAL effectors to the FokI endonuclease confer site specificity in DNA cleavage," IAPB 12th World Congress and In Vitro Biology Meeting, 4 pages, Jun. 2010.
Cole et al., "The Jpred 3 secondary structure prediction server," Nucl Acids Res, 36:W197-W201, 2008.
Cornelis, "The type III secretion injectisome," Nat Rev Microbiol, 4:811-825, 2006.
Craig et al., "Direct gene transfer in potato: a comparison of particle bombardment of leaf explants and PEG-mediated transformation of protoplasts," Plant Cell Rep, Dec. 2005, 24(10): 603-11.
Curtin et al., "Targeted mutagenesis of duplicated genes in soybean with zinc-finger nucleases," *Plant Physiology*, 156(2):466-473 (2011).
De Feyter et al., "Gene-for genes interactions between cotton R genes and Xanthomonas campestris pv. malvacearum avr genes," Mol Plant Microbe Interact, 6(2):225-237, 1993.
Defrancesco, "Move over ZFNs," Nat Biotechnol, 29: 681-684, 2011.
Denyer et al., "Granule-bound starch synthase I in isolated starch granules elongates malto-oligosaccharides processively," Biochem J, May 1999, 340: 183-91.
Desjarlais and Berg, "Toward rules relating zinc finger protein sequences and DNA binding site preferences," Proc Natl Acad Sci USA, 89:7345-7349, 1992.
Domingues et al., "The Xanthomonas citri effector protein PthA interacts with citrus proteins involved in nuclear transport, protein folding and ubiquitination associated with DNA repair," Mol Plant Pathol, 11(5):663-675, DOI : 10.1111/ J .1364-3703.2010.00636.X, 13 pages, 2010.
Doyle et al., "TAL Effector-Nucleotide Targeter (TALE-NT) 2.0: tools for TAL effector design and target prediction," Nucleic Acids Res, 40:W117-122 (2012).
Draffehn et al., "Natural diversity of potato (*Solanum tuberosum*) invertases," BMC Plant Biol., 10:271, 15 pages. (2010).
Durai et al., "Zinc finger nucleases: custom-designed molecular scissors for genome engineering of plant and mammalian cells," Nucl Acids Res, 33(1): 5978-5990, 2005.
Eisenschmidt et al., "Developing a programmed restriction endonuclease for highly specific DNA cleavage," Nucl Acids Res, 33:7039-7047, 2005.
Engler et al. "A one pot, one step, precision cloning method with high throughput capability," PLoS One, 3: e3647, 7 pages, 2008.
Engler et al., "Golden Gate Shuffling: a one-pot DNA shuffling method based on type IIs restriction enzymes," PLoS One, 4:e5553, 9 pages, 2009.
European Commission—DG Agriculture, Evaluation of the Community Policy for Starch and Starch Product, 2002, LMC International, Oxford, England, pp. 1-12.
Fajardo-Sanchez et al., "Computer design of obligate heterodimer meganucleases allows efficient cutting of custom DNA sequences," Nucl Acids Res, 36(7):2163-2173, 2008.
Foley et al., "Rapid Mutation of Endogenous Zebrafish Genes Using Zinc Finger Nucleases Made by Oligomerized Pool ENgineering (OPEN)," PLoS One, 13 pages, 4:e4348, 2009.
Fonfara et al., "Creating highly specific nucleases by fusion of active restriction endonucleases and catalytically inactive homing endonucleases," Nucl Acids Res, 40(2):847-860, 2011.
Fujikawa et al., "Suppression of defense response in plants by the avrBs3/pthA gene family of Xanthomonas spp," Mol Plant Microbe Interact, 19(3):342-349, 2006.
Gabriel et al.,"An unbiased genome-wide analysis of zinc-finger nuclease specificity," Nat Biotechnol, 29:816-823, 2011.
Gamborg et al., in: Plant Tissue Culture Methods and Applications in Agriculture, Thorpe (Ed.), Academic Press, Inc., New York, NY, 1981, pp. 115-153.
Geißler et al., "Transcriptional activators of human genes with programmable DNA-specificity," PLoS One, 6(5):e19509, May 2011.
GenBank Accession No. AAT46122, Nov. 12, 2004, 2 pages.
GenBank Accession No. ACD58243, May 19, 2008, 2 pages.
GenBank Accession No. AY986492, Jun. 24, 2005, 2 pages.
GenBank Accession No. CP000967, GI: 188518722, May 19, 2008, 606 pages.

(56) References Cited

OTHER PUBLICATIONS

GenBank Accession No. J04623, Apr. 26, 1993, 2 pages.
GenBank Accession No. M28828, Apr. 26, 1993, 3 pages.
GenBank Accession No. P14727, Jun. 28, 2011, 3 pages.
GenBank Accession No. X16130, Oct. 15, 2007, 3 pages.
Göhre and Robatzek, "Breaking the barriers: microbial effector molecules subvert plant immunity," Ann Rev Phytopathol, 46:189-215, 2008.
Gonchar et al., PspXI, a novel restriction endonuclease that recognizes the unusual DNA sequence 5'-VC↓TCGAGB-3', Bulletin of biotechnology and physico-chemical biology, 1(1):18-24, 2005, Translation by Ovchinnikov, "Science sibenzyme.com" [online], [retrieved on Aug. 11, 2011]. Retrieved from the Internet: URL: <http://science.sibenzyme.com/article8_article_3_1.phtml>, 4 pages.
Gonzalez et al., "Molecular and pathotypic characterization of new Xanthomonas oryzae strains from West Africa," Mol Plant Microbe Interact, 20(5):534-546, 2007.
Govindarajulu et al., "Evaluation of constitutive viral promoters in transgenic soybean roots and nodules," Mol. Plant Microbe Interact, 21:1027-1035 (2008).
Greiner et al., "Ectopic expression of a tobacco invertase inhibitor homolog prevents cold-induced sweetening of potato tubers," Nature Biotechnology, 17(7):708-711 (1999).
Greisman and Pabo, "A general strategy for selecting high-affinity zinc finger proteins for diverse DNA target sites," Science, 275(5300):657-661, 1997.
Gu et al., "R gene expression induced by a type-III effector triggers disease resistance in rice," Nature, 435:1122-1125 (2005).
Gu et al., "Transcription activator-like type III effector AvrXa27 depends on OsTFIIAgamma5 for the activation of Xa27 transcription in rice that triggers disease resistance to Xanthomonas oryzae pv. oryzae," Mol Plant Pathol, 10(6):829-835, 2009.
Guan et al., "Heritable endogenous gene regulation in plants with designed polydactyl zinc finger transcription factors," Proc Natl Acad Sci USA, 99(20):13296-13301, 2002.
Gürlebeck et al., "Dimerization of the bacterial effector protein AvrBs3 in the plant cell cytoplasm prior to nuclear import," Plant J, 42:175-187, 2005.
Gürlebeck et al., "Type III effector proteins from the plant pathogen Xanthomonas and their role in the interaction with the host plant," J Plant Physiol, 163(3):233-255, 2006 (Epub 2005).
Gürlebeck et al., "Visualization of novel virulence activities of the Xanthomonas type III effectors AvrBs1, AvrBs3, and AvrBs4," Mol Plant Pathol, 10(2):175-188, 2009.
Haber, "In vivo biochemistry: Physical monitoring of recombination induced by site-specific endonucleases," Bioessays, 17:609-620, 1995.
Haberlach et al., "Isolation, culture and regeneration of protoplasts from potato and several related Solanum species," Plant Science, 39:67-74 (1985).
Hahn et al., "New mechanistic insights into the virulence activity of the Xanthomonas type III effector AvrBs3," (abstract), XIV International Congress on Molecular Plant-Microbe Interactions, Quebec City, Canada, Jul. 19-23, 2009, 2 pages.
Halford et al., "The reaction mechanism of FokI excludes the possibility of targeting zinc finger nucleases to unique DNA sites," Biochem Soc Trans, 39:584-588, 2011.
Handel et al., "Expanding or restricting the target site repertoire of zinc-finger nucleases: the inter-domain linker as a major determinant of target site selectivity," Mol Ther, 17:104-111, 2009.
Haun et al., "Improved soybean oil quality by targeted mutagenesis of fatty acid desaturase 2 gene family," Plant Biotechnology Journal, 1-7 (2014).
Herbers et al., "Race-specificity of plant resistance to bacterial spot disease determined by repetitive motifs in a bacterial avirulence protein," Nature, 356:172-174, 1992.
Heuer et al., "Repeat domain diversity of avrBs3-like genes in Ralstonia solanacearum strains and association with host preferences in the field," Appl Environ Microbiol, 73(13):4379-4384, 2007.

Hockemeyer et al., "Genetic engineering of human pluripotent cells using TALE nucleases," Nat Biotechnol, 29(8):731-734, 2011.
Hopkins et al., "Identification of a family of avirulence genes from Xanthomonas oryzae pv. oryzae," Mol Plant Microbe Interact, 5(6):451-459, 1992.
Hovenkamp-Hermelink et al., "Isolation of an Amylose-Free Starch Mutant of the Potato (Solanum tuberosum L.)," Theoretical and Applied Genetics, Dec. 1987, 217-221.
Hovenkamp-Hermelink et al., "Rapid estimation of the amylose/amylopectin ratio in small amounts of tuber and leaf tissue of the potato," Potato Research 31:241-246, 1988.
Hu et al., "A virulence gene and insertion element-based RFLP as well as RAPD markers reveal high levels of genomic polymorphism in the rice pathogen Xanthomonas oryzae pv. oryzae," Syst Appl Microbiol, 30:587-600, 2007.
Huang et al., "Heritable gene targeting in zebrafish using customized TALENs," Nat Biotechnol, 29(8):699-700, 2011.
Hummel et al., "Rice gene activation by transcription activator-like effectors of Xanthomonas oryzae pvs. oryzae and oryzicola," poster presentation, and "A cipher-like mechanism governs TAL effector-DNA recognition," poster #13-517, XIV International Congress on Molecular Plant-Microbe Interactions, Quebec City, Canada, 3 pages, Jul. 19-23, 2009.
Hurt et al., "Highly specific zinc finger proteins obtained by directed domain shuffling and cell-based selection," Proc Natl Acad Sci USA, 100(21):12271-12276, 2003.
International Search Report in International Application No. PCT/IB2015/054641, dated Sep. 14, 2015, 14 pages.
Isalan et al., "A rapid, generally applicable method to engineer zinc fingers illustrated by targeting the HIV-1 promoter," Nat Biotechnol, 19(7):656-660, 2001.
Jackel et al., "Protein design by directed devolution," Annu Rev Biophys, 37:155-173, 2008.
Jones and Dangl, "The plant immune system," Nature, 444:323-329, 2006.
Jordan et al., "Physical delimitation of the pepper Bs3 resistance gene specifying recognition of the AvrBs3 protein from Xanthomonas campestris pv. vesicatoria," Theor Appl Genet, 113(5):895-905, 2006.
Kay and Bonas, "How Xanthomonas type III effectors manipulate the host plant," Curr Opin Microbiol, 12:37-43, 2009.
Kay et al., "A bacterial effector acts as a plant transcription factor and induces a cell size regulator," Science, 318:648-651 (2007).
Kay et al., "Characterization of AvrBs3-like effectors from a Brassicaceae pathogen reveals virulence and avirulence activities and a protein with a novel repeat architecture," Mol Plant Microbe Interact, 18(8):838-848, 2005.
Kay et al., "Detailed analysis of the DNA recognition motifs of the Xanthomonas type III effectors AvrBs3 and AvrBs3deltarep16," Plant J, 59(6):859-871, 2009.
Keshavarzi et al., "Basal defenses induced in pepper by lipopolysaccharides are suppressed by Xanthomonas campestris pv. vesicatoria," Mol Plant Microbe Interact, 17(7):805-815, 2004.
Kim and Chandrasegaran, "Chimeric restriction endonuclease," Proc Natl Acad Sci USA, 91(3):883-887 (Feb. 1994).
Kim et al., "Comparative analysis of three indigenous plasmids from Xanthomonas axonopodis pv. glycines," Plasmid, 56(2):79-87, 2006.
Kim et al., "Construction of a Z-DNA-specific restriction endonuclease," Proc Natl Acad Sci USA, 94(24):12875-12879, 1997.
Kim et al., "Hybrid restriction enzymes: zinc finger fusions to Fold cleavage," Proc Natl Acad Sci USA, 93:1156-1160, 1996.
Kim et al., "Site-specific cleavage of DNA—RNA hybrids by zinc finger/FokI cleavage domain fusions," Gene, 203(1):43-49, 1997.
Kim et al., "Targeted genome editing in human cells with zinc finger nucleases constructed via modular assembly," Genome Res, 19:1279-1288 (2009).
Knoop et al., "Expression of avirulence gene avrBs3 from Xanthomonas campestris pv. vesicatoria is not under the control of hrp genes and is independent of plant factors," J Bacteriol, 173(22):7142-7150, 1991.
Lahaye and Bonas, "Molecular secrets of bacterial type III effector proteins," Trends Plant Sci, 6(10):479-485, 2001.

(56) References Cited

OTHER PUBLICATIONS

Ledford, "Plant genes get fine tailoring," Nature News [online], Apr. 29, 2009 [retrieved on May 21, 2009]. Retrieved from the Internet: <URL: http://www.nature.com/news/2009/090429/full/news.2009.415.html>, 3 pages.
Lee et al., "Environmental effects on oleic acid in soybean seed oil of plant introductions with elevated oleic concentration," Crop Science, 49:1762-1768 (Sep./Oct. 2009).
Li et al., "Functional domains in FokI restriction endonuclease," Proc Natl Acad Sci USA, 89(10):4275-4279, 1992.
Li et al., "Modularly assembled designed Tal effector nucleases for targeted gene knockout and gene replacement in eukaryotes," Nucl Acids Res, 39:6315-6325, 2011.
Li et al., "TAL nucleases (TALNs): hybrid proteins composed of TAL effectors and FokI DNA-cleavage domain," Nucleic Acids Research, 39(1):359-372, 2010.
Liang et al., "Cloning and characterization of a novel avirulence gene (arp3) from Xanthomonas oryzae pv. oryzae," DNA Seq, 15(2):110-117, 2004.
Liu et al., "Design of polydactyl zinc-finger proteins for unique addressing within complex genomes," Proc Natl Acad Sci USA, 94(11):5525-5530, 1997.
Livak and Schmittgen, "Analysis of relative gene expression data using real-time quantitative PCR and the 2(-Delta C(T)) Method," *Method. Methods*, 25:402-408 (2001).
Mahfouz et al., "De novo-engineered transcription activator-like effector (TALE) hybrid nuclease with novel DNA binding specificity creates double-strand breaks," Proc Natl Acad Sci USA, 108:2623-2628, 2011.
Mahfouz et al., "TALE nucleases and next generation GM crops," GM Crops, 2(2):99-103 (Apr. 2011).
Mak, "Sequence-specific DNA-binding TALEs," Nat Biotechnol, 29:43, 2011.
Marois et al., "The xanthomonas type III effector protein AvrBs3 modulates plant gene expression and induces cell hypertrophy in the susceptible host," Mol Plant Microbe Interact, 15(7):637-646, 2002.
Miller et al., "A TALE nuclease architecture for efficient genome editing," Nat Biotechnol, 29:143-148, 2011.
Miller et al., "An improved zinc-finger nuclease architecture for highly specific genome editing," Nature Biotechnol, 25:778-785, 2007.
Minczuk et al., "Development of a single-chain, quasi-dimeric zinc-finger nuclease for the selective degradation of mutated human mitochondrial DNA," Nucleic Acids Res, 36(12):3926-3938, 2008.
Mino et al., "Efficient double-stranded DNA cleavage by artificial zinc-finger nucleases composed of one zinc-finger protein and a single-chain FokI dimer," J Biotechnol, 140(3-4):156-161, 2009.
Moore et al., "Transactivated and chemically inducible gene expression in plants," Plant J, 45:651-683, 2006.
Morbitzer et al., "Assembly of custom TALE-type DNA binding domains by modular cloning," Nucleic Acids Research, 39(13):5790-5799, 2011.
Morbitzer et al., "Regulation of selected genome loci using de novo-engineered transcription activator-like effector (TALE)-type transcription factors," Proc Natl Acad Sci U S A., 107(50):21617-21622, 2010.
Moscou and Bogdanove, "A simple cipher governs DNA recognition by TAL effectors," Science 326(5959): 1501, 2009.
Murakami et al., "The repeat domain of the type III effector protein PthA shows a TPR-like structure and undergoes conformational changes upon DNA interaction," Proteins, 78:3386-3395, 2010.
Murray and Thompson, "Rapid isolation of high molecular weight plant DNA," Nucleic Acids Res, Oct. 1980, 8(19): 4321-5.
Murray et al., "Rapid isolation of high molecular weight plant DNA," *Nucl. Acids Res*, 8(19):4321-4325 (1980).
Mussolino et al., "A novel Tale nuclease scaffold enables high genome editing activity in combination with low toxicity," *Nucleic Acids Res*, 39:9283-9293 (2011).

Nakagawa et al., "Development of series of gateway binary vectors, pGWBs, for realizing efficient construction of fusion genes for plant transformation," J Biosci Bioeng, 104:34-41, 2007.
Niño-Liu et al., "Xanthomonas oryzae pathovars: model pathogens of a model crop," Mol Plant Pathol, 7(5):303-324, 2006.
Nissan et al. "The type III effectors HsvG and HsvB of gall-forming Pantoea agglomerans determine host specificity and function as transcriptional activators." Molecular Microbiology, 61(5): 1118-1131, 2006.
Noël et al., "XopC and XopJ, two novel type III effector proteins from Xanthomonas campestris pv. vesicatoria," J Bacteriol, 185(24):7092-7102, 2003.
Ovchinnikov et al., "PspXI, a novel restriction endonuclease that recognizes the unusual DNA sequence 5-VCTCGAGB-3," Bull Biotech Physio-Chemical Biol, 2005, 1(1):18-24, retrieved from the Internet: http://science.sibenzyme.com/article8_article_3_1.phtml.
Padidam, "Chemically regulated gene expression in plants," Curr Opin Plant Biol, 6:169-177, 2003.
Paques and Duchateau, "Meganucleases and DNA Double-Strand Break-Induced recombination: Perspectives for Gene Therapy," Curr Gene Ther, 7:49-66, 2007.
Park et al., "Avirulence gene diversity of Xanthomonas axonopodis pv. Glycines isolated in Korea," J Microbiol Biotechnol, 18(9):1500-1509, 2008.
Pattanayak et al., "Revealing off-target cleavage specificities of zinc-finger nucleases by in vitro selection," Nat Methods, 8:765-770, 2011.
Paulus et al., "Silencing β1,2-xylosyltransferase in transgenic tomato fruits reveals xylose as constitutive component in IgE-binding epitopes," Frontiers in Plant Science, 2(42), 12 pages (Aug. 2011).
Pavletich and Pabo, "Zinc finger-Dna recognition: crystal structure of a Zif268-DNA complex at 2.1 A," Science, 252:809-817, 1991.
Pearson, "The fate of fingers," Nature, 455:160-164, 2008.
Pennisi, "The tale of the Tales," Science, 338(6113):1408-1411, 2012.
Pham et al., "Mutant alleles of FAD2-1A and FAD2-1B combine to produce soybeans with the high oleic acid seed oil trait," BMC Plant Biol., 10:195 (2010).
Pingoud and Silva, "Precision genome surgery," Nature Biotechnol, 25(7):743-744, 2007.
Podhajska and Szybalski, "Conversion of the FokI endonuclease to a universal restriction enzyme: cleavage of phage M13mp7 DNA at predetermined sites," Gene, 40(2-3):175-182, 1985.
Pomerantz et al., "Structure-based design of transcription factors," Science, 267(5194):93-96, 1995.
Porteus and Baltimore, "Chimeric nucleases stimulate gene targeting in human cells," Science, 300:763, 2003.
Porteus and Carroll, "Gene targeting using zinc finger nucleases," Nature Biotechnol, 23:967-973, 2005.
Porteus, "Zinc fingers on target," Nature, 459: 337-338, 2009.
Potenza et al., "Targeting transgene expression in research, agricultural, and environmental applications: Promoters used in plant transformation," In vitro Cell Dev Biol, 40(1):1-22, 2004.
Puchta et al., "Homologous recombination in plant cells is enhanced by in vivo induction of double strand breaks into DNA by a site-specific endonuclease," Nucl Acids Res, 21(22):5034-5040, 1993.
Radecke et al., "Zinc-finger nuclease-induced gene repair with oligodeoxynucleotides: wanted and unwanted target locus modifications," Mol Ther, 18(4):743-753, 2010.
Reyon et al., "Flash assembly of TALENs for high-throughput genome editing," *Nat Biotechnol*, 30:460-465 (2012).
Robson, "U.S. Enviromental Protection Agency. Starch Manufacturing: A Profile," North Carolina: Center for Economics Research, Mar. 1994.
Römer et al., "Plant pathogen recognition mediated by promoter activation of the pepper Bs3 resistance gene," Science, 318(5850):645-648 (2007).
Römer et al., "A single plant resistance gene promoter engineered to recognize multiple TAL effectors from disparate pathogens," Proc Natl Acad Sci USA, 106(48):20526-31, 2009.

(56) References Cited

OTHER PUBLICATIONS

Römer et al., "Promoter elements of rice susceptibility genes are bound and activated by specific TAL effectors from the bacterial blight pathogen, Xanthomonas oryzae pv. oryzae," New Phytol, 187:1048-1057, 2010.
Römer et al., "Recognition of AvrBs3-like proteins is mediated by specific binding to promoters of matching pepper Bs3 alleles," Plant Physiol, 150:1697-1712, 2009.
Romero et al., "Temperature sensitivity of the hypersensitive response of bell pepper to Xanthomonas axonopodis pv. vesicatoria," Phytopathology, 92(2):197-203, 2002.
Rossier et al., "HrpB2 and HrpF from Xanthomonas are type III-secreted proteins and essential for pathogenicity and recognition by the host plant," Mol Microbiol, 38(4):828-838, 2000.
Rossier et al., "The Xanthomonas HRP type III system secretes proteins from plant and mammalian bacterial pathogens," Proc Natl Acad Sci USA, 96(16):9368-9373, 1999.
Rouet et al., "Expression of a site-specific endonuclease stimulates homologous recombination in mammalian cells," Proc Natl Acad Sci USA, 91(13):6064-6068, 1994.
Rouet et al., "Introduction of double-strand breaks into the genome of mouse cells by expression of a rare-cutting endonuclease," Mol Cell Biol, 14(12):8096-8106, 1994.
Rybak et al., "Identification of Xanthomonas citri ssp. citri host specificity genes in a heterologous expression host," Mol Plant Pathol, 10(2):249-262, 2009.
Sandhu et al., "Enhanced oleic acid content in the soybean mutant M23 is associated with the deletion in the Fad2-1a gene encoding a fatty acid desaturase,"*JAOCS*, 84:229-235 (2007).
Santiago et al., "Targeted gene knockout in mammalian cells by using engineered zinc-finger nucleases," Proc Natl Acad Sci USA, 105(15):5809-5814, 2008.
Scholze and Boch, "TAL effectors are remote controls for gene activation," Curr Opin Microbiol, 14:47-53, 2011.
Scholze and Boch. "TAL effector-DNA specificity," Virulence, 1(5):428-432, 2010.
Schornack et al., "Characterization of AvrHah1, a novel AvrBs3-like effector from Xanthomonas gardneri with virulence and avirulence activity," New Phytol, 179:546-556, 2008.
Schornack et al., "Expression levels of avrBs3-like genes affect recognition specificity in tomato Bs4—but not in pepper BS3-mediated perception," Mol Plant-Microbe Interact, 18(11):1215-1225, 2005.
Schornack et al., "Gene-for-gene-mediated recognition of nuclear-targeted AvrBs3-like bacterial effector proteins," J. Plant Physiol, 163:256-272 (2006).
Schornack et al., "The tomato resistance protein Bs4 is a predicted non-nuclear TIR-NB-LRR protein that mediates defense responses to severely truncated derivatives of AvrBs4 and overexpressed AvrBs3," Plant J, 37(1):46-60, 2004.
Segal et al., "Endonuclease-induced, targeted homologous extrachromosomal recombination in Xenopus oocytes," Proc Natl Acad Sci USA, 92(3):806-810, 1995.
Sera, "Inhibition of virus DNA replication by artificial zinc finger proteins," J Virol, 79(4):2614-2619, 2005.
Shepard and Totten, "Mesophyll cell protoplasts of potato: isolation, proliferation, and plant regeneration," Plant Physiol., 60:313-316(1977).
Shepard, in: Genetic Improvement of Crops/Emergent Techniques, Rubenstein, Gengenbach, Philips, and Green (Eds.), Univ. of Minnesota Press, Minneapolis, MN, 1980, pp. 185-219.
Shevelev et al., "The TREX2 3'→5' exonuclease physically interacts with DNA polymerase delta and increases its accuracy," Scientific World Journal, Feb. 2002, 2: 275-81.
Shukla et al., "Precise genome modification in the crop species *Zea mays* using zinc-finger nucleases," Nature, 459(7245):437-441, 2009.
Simon et al., "Targeting DNA with triplex-forming oligonucleotides to modify gene sequence," Biochimie, 90:1109-1116, 2008.

Skipper, "Technology: The holy grail for plant biologists," Nature Reviews Genetics, 10(6):350, 2009.
Strasser et al., "Generation of glycol-engineered *Nicotiana bethamiana* for the production of monoclonal antibodies with a homogeneous human-like N-glycan structure," Plant Biotechnology Journal, 6:392-402 (2008).
Studholme et al., "Genome-wide sequencing data reveals virulence factors implicated in banana Xanthomonas wilt," FEMS Microbiol Lett., 310(2):182-192, 2010.
Sugio et al., "Two type III effector genes of Xanthomonas oryzae pv. oryzae control the induction of the host genes OsTFIIAgammal and OsTFX1 during bacterial blight of rice," Proc Natl Acad Sci USA, 104:10720-10725 (2007).
Swarup et al., "An Xanthomonas citri pathogenicity gene, pthA, pleiotropically encodes gratuitous avirulence on nonhosts," Mol Plant Microbe Interact, 5(3):204-213, 1992.
Szurek et al. "Type III-dependent translocation of the Xanthomonas AvrBs3 protein into the plant cell," Mol Microbiol, 46(1): 13-23, 2002.
Szurek et al., "Eukaryotic features of the Xanthomonas type III effector AvrBs3: protein domains involved in transcriptional activation and the interaction with nuclear import receptors from pepper," Plant J, 26(5):523-534, 2001.
Takenaka et al., "Inhibition of tomato yellow leaf curl virus replication by artificial zinc-finger proteins," Nucl Acids Symposium Series, 51(1):429-430, 2007.
Thieme et al., "New type III effectors from Xanthomonas campestris pv. vesicatoria trigger plant reactions dependent on a conserved N-myristoylation motif," Mol Plant Microbe Interact, 20(10):1250-1261, 2007.
Thierry et al., "Cleavage of yeast and bacteriophage T7 genomes at a single site using the rare cutter endonuclease I-Sce I," Nucl Acids Res, 19(1):189-190, 1991.
Tovkach et al., "A toolbox and procedural notes for characterizing novel zinc finger nucleases for genome editing in plant cells," Plant J, 57:747-757, 2009.
Townsend et al., "High-frequency modification of plant genes using engineered zinc-finger nucleases," Nature, 459:442-445, 2009.
Urnov et al., "Highly efficient endogenous human gene correction using designed zinc-finger.nuclease," Nature, 435(7042):646-651, 2005.
Van Den Ackerveken et al., "Recognition of the bacterial avirulence protein AvrBs3 occurs inside the host plant cell," Cell, 87(7):1307-1316, 1996.
Van Den Elzen et al., "A chimaeric hygromycin resistance gene as a selectable marker in plant cells," Plant Molecular Biology, 5:299-302 (1985).
Vergunst et al., "VirB/D4-Dependent Protein Translocation from *Agrobacterium* into Plant Cells," Science, 290:979-982, 2000.
Visser et al., "Inhibition of the expression of the gene for granule-bound starch synthase in potato by antisense constructs," Mol Gen Genet MGG. Feb. 1991, 225(2):289-296.
Voytas et al., "Plant genome engineering with sequence-specific nucleases," Ann Rev Plant Biol, Apr. 2013, 327-350.
Voytas et al., "Plant science. DNA binding made easy," Science, 326(5959):1491-1492, 2009.
Wah et al., "Structure of FokI has implications for DNA cleavage," Proc Natl Acad Sci USA, 95(18):10564-10569, 1998.
Wah et al., "Structure of the multimodular endonuclease FokI bound to DNA," Nature, 388(3):97-100, 1997.
Wang et al., "Chemically regulated expression systems and their applications in transgenic plants," Transgenic Res, 12:529-540, 2003.
Weber et al., "The type III-dependent Hrp pilus is required for productive interaction of Xanthomonas campestris pv. vesicatoria with pepper host plants," J Bacteriol, 187(7):2458-2468, 2005.
White and Yang, "Host and pathogen factors controlling the rice/Xanthomonas oryzae interaction," Plant Physiol, 150:1677-1686, 2009.
White et al., "The type III effectors of Xanthomonas," Mol Plant Pathol, 10:749-766, 2009.
Wright et al., "High-frequency homologous recombination in plants mediated by zinc-finger nucleases," *Plant J*, 44:693-705 (2005).

(56) References Cited

OTHER PUBLICATIONS

Yang and White, "Diverse members of the AvrBs3/PthA family of type III effectors are major virulence determinants in bacterial blight disease of rice," Mol Plant Microbe Interact, 17(11):1192-1200, 2004.

Yang et al. "The virulence factor AvrXa7 of Xanthomonas olyzae of Oryzae is a type III secretion pathway-dependent nuclear-localized double stranded DNA binding protein," Proc Natl Acad Sci USA, 97(17): 9807-9812, 2000.

Yang et al., "Avoidance of host recognition by alterations in the repetitive and C-terminal regions of AvrXa7, a type III effector of Xanthomonas oryzae pv. oryzae," Mol Plant Microbe Interact, 18(2):142-149, 2005.
Yang et al., "Os8N3 is a host disease-susceptibility gene for bacterial blight of rice," *Proc Natl Acad Sci USA*, 103:10503-10508 (2006).
Yoo et al., "*Arabidopsis* mesophyll protoplasts: a versatile cell system for transient gene expression analysis," Nature Protocols, 2:1565-1572 (2007).
Yuan et al., "Characterization of Xanthomonas olyzae-responsive cis-acting element in the promoter of rice race-specific susceptibility gene Xa13," Mol Plant, 4(2):300-309, 2011.
Zeeman et al., "Starch: its metabolism, evolution, and biotechnological modification in plants," Annu Rev Plant Biol, 2010, 61: 209-34.
Zhang et al., "Efficient construction of sequence-specific TAL effectors for modulating mammalian transcription.," Nat Biotechnol, 29:149-153 (2011).
Zhang et al., "High frequency targeted mutagenesis in *Arabidopsis thaliana* using zinc finger nucleases," Proc Natl Acad Sci USA, 107(26):12028-12033 (2010).
Zhang et al., "RNAi effects on regulation of endogenous acid invertase activity in potato (*Solanum tuberosum* L.) tubers," Chin J Agric. Biotechnol, 5:107-111 (2008).
Zhang et al., "Transcription activator-like effector nucleases enable efficient plant genome engineering," Plant Physiology, Nov. 2012, 161(1): 20-27.
Zhu et al., "The C terminus of AvrXa10 can be replaced by the transcriptional activation domain of VP16 from the herpes simplex virus," Plant Cell, 11(9):1665-1674, 1999.
Zhu et al., "AvrXa10 Contains an Acidic Transcriptional Activation Domain in the Functionally Conserved C Terminus," Molecular Plant-Microbe Interactions, 11(8): 824-832, 1998.
Zhu et al., "The rsma-like gene rsmA(XOO) of Xanthomonas oryzae pv. oryzae regulates bacterial virulence and production of diffusible signal factor," Mol Plant Pathol, 12(3):227-237, 2011, Epub 2010.
Zou et al., "Identification of an avirulence gene, avrxa5, from the rice pathogen Xanthomonas oryzae pv. oryzae," Sci China Life Sci, 53(12):1440-1449, 2010.
Zrenner et al., "Soluble acid intervase determines the hexos-to sucrose ratio in cold-stored potato tubers," Planta, 198(2):246-252 (1996).
Zuo and Chua, "Chemical-inducible systems for regulated expression of plant genes," Curr Opin Biotechnol, 11:146-151, 2000.
Zuo et al., "Technical advance: an estrogen receptor-based transactivator XVE mediates highly inducible gene expression in transgenic plants," Plant J. 24:265-273 (2000).
International Preliminary Report on Patentability in International Application No. PCT/162015/054641, dated Dec. 29, 2016, 10 pages.
Niemirowicz-Szczytt, "Excessive homozygosity in doubled haploids—advantages and disadvantages for plant breeding and fundamental research," *Physiologiae plantarum*., 19(2):155-167, 1997.
Van der Leij et al., "Sequence of the structural gene for granule-bound starch synthase of potato (*Solanum tuberosum* L.) and evidence for a single point deletion in the amfallele," *Mol Gen Genet*., 228:240-248, 1991.

* cited by examiner

FIG. 1

GBSS_T1
actctgactcacaatggtttaagggctgttaacaagcttgatgggctccaatcaagaactaatactaaggtaacacccaag
atggcatccagaactgagaccaagagaccggatgctcagctaccattgttgtggaaaggaatgaacttgatctttgtg
ggtactgaggttggtccttggagcaaaactggtgactaggtgatgtcttggtggactaccaccagccctgcagta
(SEQ ID NO:1)

FIG. 2

S. tuberosum GBSS complete CDS; GenBank EU403426.2

ATGGCAAGCATCACAGCTTCACACCACTTTGTGTCAAGAAGCCAAACTTCACTAGACACCAAATCAACCTTGTCACAGATA
GGACTCAGGAACCATACTCTGACTCTCACAATGGTTAAGGCTGTGTTAACAAGCTTGATGGGCTCCAATCAAGAACTAATACT
AAGGTAACACCCAAGATGGCATCCAAGAGACCTGGATGCTCAGCTACCATTGTTGTGGAAAGGAATG
AACTTGATCTTTGTGGGTACTGAGGTTGGTCCTTGGAGCAAAACTGGTGGACTAGGTGATGTTCTTGGTGGACTACCACCA
GCCCTTGCAGCCCGCGGACATCGGGTAATGACAATATCCCCCCGTTATGACCAATACAAAGATGCTTGGGATACTAGCGTT
GCGGTTGAGGTCAAAGTTGGAGACAGCATTGAAAATTGTTCGTTTCTTCACTGCTATAAACGTGGGGTTGATCGTGTTTT
GTTGACCACCCAATGTTCTTGGAGAAAGTTTGGGGCAAAACTGGTTCAAAAATCTATGCCCCAAAGCTGGACTAGATTAT
CTGGACAATGAACTTAGGTTCAGCTTGTTGTGTCAAGCAGCCCTAGAGGCACCTAAAGTTTTGAATTGAACAGTAGCAAC
TACTTCTCAGGACCATATGGAGAGGATGTTCTCTTCATTGCCAATGATTGGCACACAGCTCTCATTCCTGCTACTTGAAG
TCAATGTACCAGTCCAGAGAATCTATTTGAATGCCAAGGTCGCTTTCTGCATCCATAACATTGCCTACCAAGGCCGATTT
TCTTTCTCTGACTTCCCTCTTCCTGATGAATTCAGGGGTTCTTTGATTTCATTGATGGATATGAGAAGCCT
GTTAAGGGTAGGAAAATCAACTGGATGAAGGCTGGGATATTAGAATCACATAGGGTGGTTACAGTGAGCCCATACTATGCC
CAAGAACTTGTCTCTGTGTTGACAAGGTTCATAACCAGCTGCATAACTGCATAATACCACTGTCATGGACGCA
GGCATGGATACACAAGAGTGGAACCAGCTCTTCAAGCAGCAGTTGGCTTGCAGAGATCCCTTTGATTGGCTTCATCGGC
AAACCTTTACTAAAGGAGGCTTCAGATAATCTTGTTGCTGCAATTCACCAAGTTCATCGGATTGGATGTTCAAATTGTAGTC
AGACTTGAGGAGCAGAAAGTTCAGATATTGAGCAGGAGATTGAACAGCTGTTGTACCCTAACAAAGCTAAAGGAGTGGCA
CTTGGAACTGGCAAATGTCCCCTTTGGCTTCACATGATGCAGTTTGAGCAGGACATGCTGCTGTGTCAAGCAGATTGAACCTTGTGT
AAATTCAATGTCCCTTTGGCTTCACATGATGCAGTTGCCAATCTGTGCATCGACTGGTTGCTTGTTGACACTGTGAAAGAA
CTCATTCAGTTACATGCCGATATGCAGTGCAACAGTGCCAATGTTGAATCGCGATGTTAAGCCCAGCTGATGTGCTTAAGATAGTAACA
GGCTATACTGGATTCCATATGGGAGCCTTCAATGTTGAATGCGATGTTGTTGACCAGCTGATGTGCTTAAGATAGTAACA
ACAGTGCTAGAGCTCTTGAGCCAGTCTAGCACCCCTCGCCATTTGCTGAGATGATAAAAAATTGCATGTCAGAGGAACTCTCC
TGGAAGGAACCTGCCAAGAAATGGGAGACATTGCTATTGGGCTTAGGAGCTTCTGGCAGTGAACCCGGTGTTGAAGGGAA
GAAATCGCTCCACTTGCCAAGGAAAATGTAGCCACTCCCTAA (SEQ ID NO:4)

FIG. 3

GBSS_T1 2dpt

| Sequence | Number of Deletions | SEQ ID NO: |
|---|---|---|
| TCTGACTCACAATGGTTTAAGGGGCTGTTAACAAGCTTGATGGGCTCCAA | 0 | 5 |
| TCTGACTCACAATGGTTTAAGGT-----AACAAGCTTGATGGGCTCCAA | 5 | 6 |
| TCTGACTCACAATGGTTTAATTA------ACAAGCTTGATGGGCTCCAA | 6 | 7 |
| TCTGACTCACAATGGTTTA--------TAACAAGCTTGATGGGCTCCAA | 8 | 8 |
| TCTGACTCACAATGGTTTA----------ACAAGCTTGATGGGCTCCAA | 10 | 9 |

GBSS_T1 + TREX2 2dpt

| Sequence | Number of Deletions | SEQ ID NO: |
|---|---|---|
| TCTGACTCACAATGGTTTAAGGGGCTGTTAACAAGCTTGATGGGCTCCAA | 0 | 5 |
| TCTGACTCACAATGGTTTAAG------TAACAAGCTTGATGGGCTCCAA | 6 | 10 |
| TCTGACTCACAATGGTTTAAGGA-------CAAGCTTGATGGGCTCCAA | 7 | 11 |
| TCTGACTCACAATGGTTT---------TAACAAGCTTGATGGGCTCCAA | 9 | 12 |
| TCTGACTCACAATGGTTT----------AACGAGCGTGATGGGCTCCGA | 10 | 13 |

FIG. 4A

Plant: St226-1

| | | Number of reads/total reads | SEQ ID NO: |
|---|---|---|---|
| TCTGACTCACAATGGTTTAAGGGCTGTTAACAAGCTTGATGGGCTCCAA | WT | 3/7 | 5 |
| TCTGACTCACAATGGTTTAAGGGCT---AACAAGCTTGATGGGCTCCAA | -3 | 1/7 | 14 |
| TCTGACTCACAATGGTTTAAGGGCT--------GTTTGATGGGCTCCAA | -8 | 1/7 | 15 |
| TCTGACTCACAATGGTTTAAGGG-----AACAAGCTTGATGGGCTCCAA | -5 | 2/7 | 16 |

Plant: St226-2

| | | Number of reads/total reads | SEQ ID NO: |
|---|---|---|---|
| TCTGACTCACAATGGTTTAAGGGCTGTTAACAAGCTTGATGGGCTCCAA | WT | 3/7 | 5 |
| TCTGACTCACAATGGTTTAAGGGCT---AACAAGCTTGATGGGCTCCAA | -3 | 2/7 | 14 |
| TCTGACTCACAATGGTTTAAGGGCT--------GTTTGATGGGCTCCAA | -8 | 2/7 | 15 |

Plant: St226-4

| | | Number of reads/total reads | SEQ ID NO: |
|---|---|---|---|
| TCTGACTCACAATGGTTTAAGGGCTGTTAACAAGCTTGATGGGCTCCAA | WT | 4/8 | 5 |
| TCTGACTCACAATGGTTTAAGGGCT--------GTTTGATGGGCTCCAA | -8 | 3/8 | 15 |
| TCTGACTCACAATGGTTTAAGGG-----AACAAGCTTGATGGGCTCCAA | -5 | 1/8 | 16 |

FIG. 4B

Plant: St226-5

| Sequence | | Number of reads/total reads | SEQ ID NO: |
|---|---|---|---|
| TCTGACTCACAATGGTTTAAGGGCTGTGTTAACAAGCTTGATGGGCTCCAA | WT | 1/8 | 5 |
| TCTGACTCACAATGGTTTAAGGGCT---AACAAGCTTGATGGGCTCCAA | -3 | 1/8 | 14 |
| TCTGACTCACAATGGTTTAAGGGCT--------GTTTGATGGGCTCCAA | -8 | 4/8 | 15 |
| TCTGACTCACAATGGTTTAAGGG-----AACAAGCTTGATGGGCTCCAA | -5 | 2/8 | 16 |

Plant: St226-6

| Sequence | | Number of reads/total reads | SEQ ID NO: |
|---|---|---|---|
| TCTGACTCACAATGGTTTAAGGGCTGTGTTAACAAGCTTGATGGGCTCCAA | WT | 3/8 | 5 |
| TCTGACTCACAATGGTTTAAGGGCT---AACAAGCTTGATGGGCTCCAA | -3 | 2/8 | 14 |
| TCTGACTCACAATGGTTTAAGGGCT--------GTTTGATGGGCTCCAA | -8 | 1/8 | 15 |
| TCTGACTCACAATGGTTTAAGGG-----AACAAGCTTGATGGGCTCCAA | -5 | 2/8 | 16 |

Plant: St226-9

| Sequence | | Number of reads/total reads | SEQ ID NO: |
|---|---|---|---|
| TCTGACTCACAATGGTTTAAGGGCTGTGTTAACAAGCTTGATGGGCTCCAA | WT | 1/8 | 5 |
| TCTGACTCACAATGGTTTAAGGGCT---AACAAGCTTGATGGGCTCCAA | -3 | 4/8 | 14 |
| TCTGACTCACAATGGTTTAAGGGCT--------GTTTGATGGGCTCCAA | -8 | 2/8 | 15 |
| TCTGACTCACAATGGTTTAAGGG-----AACAAGCTTGATGGGCTCCAA | -5 | 1/8 | 16 |

FIG. 5

```
Plant: St226-8                                                                      Number of
                                                                                    reads/total reads    SEQ ID NO:
TCTGACTCACAATGGTTTAAGGCT---AACAAGCTTGATGGGCTCCAA    -3                              2/7                  14
TCTGACTCACAATGGTTTAAGGCT-------GTTTGATGGGCTCCAA     -8                              3/7                  15
-------------------------------AAGCTTGATGGGCTCCAA   -31                             2/7                  17
```

`US 10,301,637 B2`

SEQUENCE LISTING

<160> NUMBER OF SEQ ID NOS: 18

<210> SEQ ID NO 1
<211> LENGTH: 240
<212> TYPE: DNA
<213> ORGANISM: Solanum tuberosum

```
<400> SEQUENCE: 1
actctgactc acaatggttt aagggctgtt aacaagcttg atgggctcca atcaagaact      60
aatactaagg taacacccaa gatggcatcc agaactgaga ccaagagacc tggatgctca     120
gctaccattg tttgtggaaa gggaatgaac ttgatctttg tgggtactga ggttggtcct     180
tggagcaaaa ctggtggact aggtgatgtt cttggtggac taccaccagc ccttgcagta     240

<210> SEQ ID NO 2
<211> LENGTH: 17
<212> TYPE: DNA
<213> ORGANISM: Solanum tuberosum

<400> SEQUENCE: 2
tctgactcac aatggtt                                                     17

<210> SEQ ID NO 3
<211> LENGTH: 17
<212> TYPE: DNA
<213> ORGANISM: Solanum tuberosum

<400> SEQUENCE: 3
agcttgatgg gctccaa                                                     17

<210> SEQ ID NO 4
<211> LENGTH: 1824
<212> TYPE: DNA
<213> ORGANISM: Solanum tuberosum

<400> SEQUENCE: 4
atggcaagca tcacagcttc acaccacttt gtgtcaagaa gccaaacttc actagacacc      60
aaatcaacct tgtcacagat aggactcagg aaccatactc tgactcacaa tggtttaagg     120
gctgttaaca agcttgatgg gctccaatca agaactaata ctaaggtaac acccaagatg     180
gcatccagaa ctgagaccaa gagacctgga tgctcagcta ccattgtttg tggaaaggga     240
atgaacttga tctttgtggg tactgaggtt ggtccttgga gcaaaactgg tggactaggt     300
gatgttcttg gtggactacc accagccctt gcagcccgcg acatcgggt aatgacaata     360 tccccccgtt atgaccaata caaagatgct tgggatacta gcgttgcggt tgaggtcaaa     420
gttggagaca gcattgaaat tgttcgtttc tttcactgct ataaacgtgg ggttgatcgt     480
gtttttgttg accacccaat gttcttggag aaagtttggg gcaaaactgg ttcaaaaatc     540
tatggcccca aagctggact agattatctg gacaatgaac ttaggttcag cttgttgtgt     600
caagcagccc tagaggcacc taaagttttg aatttgaaca gtagcaacta cttctcagga     660
ccatatggag aggatgttct cttcattgcc aatgattggc acacagctct cattccttgc     720
tacttgaagt caatgtacca gtccagagga atctatttga atgccaaggt cgctttctgc     780
atccataaca ttgcctacca aggccgattt tcttttctctg acttccctct tctcaatctt     840
cctgatgaat tcagggggttc ttttgatttc attgatggat atgagaagcc tgttaagggg     900
aggaaaatca actggatgaa ggctgggata ttagaatcac atagggtggt tacagtgagc     960
ccatactatg cccaagaact tgtctctgct gttgacaagg tgttgaatt ggacagtgtc    1020 cttcgtaaga cttgcataac tgggattgtg aatggcatgg atacacaaga gtggaaccca    1080
gcgactgaca aatacacaga tgtcaaatac gatataacca ctgtcatgga cgcaaaacct    1140
ttactaaagg aggctcttca agcagcagtt ggcttgcctg ttgacaagaa gatcccttg    1200 attggcttca tcggcagact tgaggagcag aaaggttcag atattcttgt tgctgcaatt    1260
```

```
cacaagttca tcggattgga tgttcaaatt gtagtccttg gaactggcaa aaaggagttt    1320
gagcaggaga ttgaacagct cgaagtgttg taccctaaca aagctaaagg agtggcaaaa    1380
ttcaatgtcc ctttggctca catgatcact gctggtgctg attttatgtt ggttccaagc    1440
agatttgaac cttgtggtct cattcagtta catgctatgc gatatggaac agtgccaatc    1500
tgtgcatcga ctggtggact tgttgacact gtgaaagaag ctatactgg attccatatg    1560 ggagccttca atgttgaatg cgatgttgtt gacccagctg atgtgcttaa gatagtaaca    1620
acagttgcta gagctcttgc agtctatggc accctcgcat ttgctgagat gataaaaaat    1680
tgcatgtcag aggaactctc ctggaaggaa cctgccaaga atgggagac attgctattg     1740 ggcttaggag cttctggcag tgaacccggt gttgaagggg aagaaatcgc tccacttgcc    1800
aaggaaaatg tagccactcc ctaa                                          1824

<210> SEQ ID NO 5
<211> LENGTH: 49
<212> TYPE: DNA
<213> ORGANISM: Solanum tuberosum

<400> SEQUENCE: 5
tctgactcac aatggtttaa gggctgttaa caagcttgat gggctccaa               49

<210> SEQ ID NO 6
<211> LENGTH: 45
<212> TYPE: DNA
<213> ORGANISM: Artificial Sequence
<220> FEATURE:
<223> OTHER INFORMATION: mutant, experimentally generated

<400> SEQUENCE: 6
ttctgactca caatggttta aggtaacaag cttgatgggc tccaa                   45

<210> SEQ ID NO 7
<211> LENGTH: 43
<212> TYPE: DNA
<213> ORGANISM: Artificial Sequence
<220> FEATURE:
<223> OTHER INFORMATION: mutant, experimentally generated

<400> SEQUENCE: 7
tctgactcac aatggtttaa ttaacaagct tgatgggctc caa                     43

<210> SEQ ID NO 8
<211> LENGTH: 41
<212> TYPE: DNA
<213> ORGANISM: Artificial Sequence
<220> FEATURE:
<223> OTHER INFORMATION: mutant, experimentally generated

<400> SEQUENCE: 8
tctgactcac aatggtttat aacaagcttg atgggctcca a                       41

<210> SEQ ID NO 9
<211> LENGTH: 39
<212> TYPE: DNA
<213> ORGANISM: Artificial Sequence
<220> FEATURE:
<223> OTHER INFORMATION: mutant, experimentally generated

<400> SEQUENCE: 9
tctgactcac aatggtttaa caagcttgat gggctccaa                          39
```

```
<210> SEQ ID NO 10
<211> LENGTH: 43
<212> TYPE: DNA
<213> ORGANISM: Artificial Sequence
<220> FEATURE:
<223> OTHER INFORMATION: mutant, experimentally generated

<400> SEQUENCE: 10
tctgactcac aatggtttaa gtaacaagct tgatgggctc caa          43

<210> SEQ ID NO 11
<211> LENGTH: 42
<212> TYPE: DNA
<213> ORGANISM: Artificial Sequence
<220> FEATURE:
<223> OTHER INFORMATION: mutant, experimentally generated

<400> SEQUENCE: 11
tctgactcac aatggtttaa ggacaagctt gatgggctcc aa           42

<210> SEQ ID NO 12
<211> LENGTH: 40
<212> TYPE: DNA
<213> ORGANISM: Artificial Sequence
<220> FEATURE:
<223> OTHER INFORMATION: mutant, experimentally generated

<400> SEQUENCE: 12
tctgactcac aatggtttta acaagcttga tgggctccaa              40

<210> SEQ ID NO 13
<211> LENGTH: 39
<212> TYPE: DNA
<213> ORGANISM: Artificial Sequence
<220> FEATURE:
<223> OTHER INFORMATION: mutant, experimentally generated

<400> SEQUENCE: 13
tctgactcac aatggtttaa cgagcgtgat gggctccga                39

<210> SEQ ID NO 14
<211> LENGTH: 46
<212> TYPE: DNA
<213> ORGANISM: Artificial Sequence
<220> FEATURE:
<223> OTHER INFORMATION: mutant, experimentally generated

<400> SEQUENCE: 14
tctgactcac aatggtttaa gggctaacaa gcttgatggg ctccaa       46

<210> SEQ ID NO 15
<211> LENGTH: 41
<212> TYPE: DNA
<213> ORGANISM: Artificial Sequence
<220> FEATURE:
<223> OTHER INFORMATION: mutant, experimentally generated

<400> SEQUENCE: 15
tctgactcac aatggtttaa gggctgtttg atgggctcca a            41

<210> SEQ ID NO 16
<211> LENGTH: 44
<212> TYPE: DNA
<213> ORGANISM: Artificial Sequence
<220> FEATURE:
<223> OTHER INFORMATION: mutant, experimentally generated
```

```
<400> SEQUENCE: 16
tctgactcac aatggtttaa gggaacaagc ttgatgggct ccaa                    44

<210> SEQ ID NO 17
<211> LENGTH: 18
<212> TYPE: DNA
<213> ORGANISM: Artificial Sequence
<220> FEATURE:
<223> OTHER INFORMATION: mutant, experimentally generated

<400> SEQUENCE: 17
aagcttgatg ggctccaa                                                 18

<210> SEQ ID NO 18
<211> LENGTH: 9
<212> TYPE: PRT
<213> ORGANISM: Artificial Sequence
<220> FEATURE:
<223> OTHER INFORMATION: consensus

<400> SEQUENCE: 18

Leu Ala Gly Leu Ile Asp Ala Asp Gly
1               5
```

POTATOES WITH REDUCED GRANULE-BOUND STARCH SYNTHASE

CROSS-REFERENCE TO RELATED APPLICATIONS

This application is claims benefit of priority from U.S. Provisional Application No. 62/014,808, filed on Jun. 20, 2014.

TECHNICAL FIELD

This document provides materials and methods for creating potato varieties with reduced granule bound starch synthase.

BACKGROUND

The world starch market was estimated to be 48.5 million tons in 2000, with an output value of 20 billion dollars per year. Only about 5% of the global starch supply (2.6 million tons) is obtained from potatoes (European Commission—DG Agriculture, *Evaluation of the Community Policy for Starch and Starch Product,* 2002, LMC INTERNATIONAL, Oxford, England, pp. 1-12). Potato tuber starch is mainly composed of two polymers—amylopectin and amylose. The different physiochemical properties of these two molecules can require costly processing before the starch is amenable to industrial processes.

SUMMARY

This document provides materials and methods for creating potato varieties that have reduced granule-bound starch synthase (GBSS). GBSS is an enzyme involved in the synthesis of amylose, and reduced levels of GBSS therefore can result in starch that contains a reduced proportion of amylose and a comparatively higher proportion of amylopectin. Potato varieties having such modified starch are also provided.

The disclosure herein is based at least in part on the discovery that potatoes having reduced GBSS can be obtained, without the use of transgenesis, using a sequence-specific nuclease to make a targeted mutation or knockout in the GBSS gene. The modified potatoes can have improved starch characteristics for particular industrial purposes, as compared to non-modified potatoes. Further, the potatoes do not carry any foreign DNA and therefore may not be considered by regulatory agencies as a transgenic or genetically modified (GM) crop. This document also is based at least in part on the development of potato cultivars with loss-of-function GBSS mutations that are created by sequence-specific nucleases.

In one aspect, this document features a *Solanum* plant, plant part, or plant cell containing a mutation in at least two (e.g., at least three) granule-bound starch synthase (GBSS) alleles endogenous to the plant, plant part, or plant cell, such that the plant, plant part, or plant cell has reduced expression of GBSS as compared to a control *Solanum* plant, plant part, or plant cell that lacks the mutation. Each mutation can be a deletion of more than one nucleotide base pair, and can be at a target sequence as set forth in SEQ ID NO:4, at a target sequence having at least 95 percent identity to SEQ ID NO:4, at a target sequence as set forth in SEQ ID NO:1, or at a target sequence having at least 95 percent identity to SEQ ID NO:1.

The plant, plant part, or plant cell can be made using a rare-cutting endonuclease (e.g., a transcription activator-like effector endonuclease (TALE-nuclease)). The TALE-nuclease can bind to a sequence as set forth in SEQ ID NO:2 or SEQ ID NO:3, for example. Each of the at least two GBSS alleles can exhibit removal of an endogenous nucleic acid, without including any exogenous nucleic acid. Every endogenous GBSS allele may be mutated, and may exhibit removal of an endogenous nucleic acid without including any exogenous nucleic acid. The plant, plant part, or plant cell may have no detectable expression of GBSS.

The *Solanum* plant, plant part, or plant cell can be, for example a *S. tuberosum* plant, plant part, or plant cell. The plant, plant part, or plant cell can have decreased levels of amylose as compared to a control plant, plant part, or plant cell that lacks the mutation.

In another aspect, this document features a method for making a *Solanum* plant. The method can include (a) contacting a population of *Solanum* plant cells containing a functional GBSS allele with a rare-cutting endonuclease targeted to an endogenous GBSS sequence, (b) selecting from the population a cell in which at least two (e.g., at least three) GBSS alleles have been inactivated, and (c) growing the selected plant cell into a *Solanum* plant, wherein the *Solanum* plant has reduced levels of amylose as compared to a control *Solanum* plant in which the at least two GBSS alleles have not been inactivated. The *Solanum* plant cells can be, for example, protoplasts. The method can include transforming the population of plant cells with a nucleic acid (e.g., an mRNA or a vector) encoding the rare-cutting endonuclease, or introducing into the population of plant cells a rare-cutting endonuclease protein.

In some embodiments, the rare-cutting endonuclease can be a TALE-nuclease (e.g, a TALE-nuclease targeted to a sequence as set forth in SEQ ID NO:4, to a sequence having at least 95 percent identity to the sequence set forth in SEQ ID NO:4, to a sequence as set forth in SEQ ID NO:1, or to a sequence having at least 95 percent identity to the sequence set forth in SEQ ID NO:1. The TALE-nuclease can bind to a sequence as set forth in SEQ ID NO:2 or SEQ ID NO:3.

The method can further include culturing the selected plant cells to generate plant lines, and/or isolating genomic DNA containing at least a portion of the GBSS locus from the plant cells. In some cases, the *Solanum* plant cells are *S. tuberosum* plant cells.

In still another aspect, this document features a method for producing a starch product. The method can include (a) providing a *Solanum* plant or plant part that contains a mutation in at least two (e.g., at least three) GBSS alleles endogenous to the plant or plant part, such that the plant, plant part, or plant cell has reduced expression of GBSS as compared to a control *Solanum* plant or plant part that lacks the mutation, and (b) producing a starch product from the plant or plant part. Each said mutation can be at a target sequence as set forth in SEQ ID NO:4, at a target sequence having at least 95 percent identity to SEQ ID NO:4, at a target sequence as set forth in SEQ ID NO:1, or at a target sequence having at least 95 percent identity to SEQ ID NO:1. Each mutation can be made using a rare-cutting endonuclease (e.g., a TALE-nuclease, such as a TALE-nuclease that binds to a sequence as set forth in SEQ ID NO:2 or SEQ ID NO:3). The *Solanum* plant or plant part can be a *S. tuberosum* plant or plant part, and may have no detectable expression of granule-bound starch synthase.

This document also features a starch product produced from a *Solanum* plant or plant part that contains a mutation in each GBSS allele endogenous to the plant or plant part, such that the plant, plant part, or plant cell has no functional GBSS allele. Each mutation can be at a target sequence as set forth in SEQ ID NO:4, at a target sequence having at least 95 percent identity to SEQ ID NO:4, at a target sequence as set forth in SEQ ID NO:1, or at a target sequence having at least 95 percent identity to SEQ ID NO:1. Each mutation can be made using a rare-cutting endonuclease (e.g., a TALE-nuclease). The TALE-nuclease can bind to a sequence as set forth in SEQ ID NO:2 or SEQ ID NO:3. The starch product can have decreased levels of amylose as compared to a starch product made from a control plant or plant part that lacks the mutation. The *Solanum* plant or plant part can be a *S. tuberosum* plant or plant part, and the starch product can be a reduced-amylose starch.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 shows a representative DNA sequence (SEQ ID NO:1) from a GBSS gene. The underlined sequences (SEQ ID NOS:2 and 3) represent target sites for TALE-nucleases that recognize the GBSS gene.

FIG. 2 shows the DNA sequence of a naturally occurring *S. tuberosum* GBSS nucleotide sequence (SEQ ID NO:4).

FIG. 3 shows examples of TALE-nuclease-induced mutations in the GBSS gene. The top line of each panel shows the DNA sequence of the recognition site for the GBSS TALE-nucleases (underlined). The other sequences show representative mutations that were induced by imprecise non-homologous end joining (NHEJ). Deletion sizes are given on the right.

FIGS. 4A and 4B show examples of six individual plant genotypes that contain TALE-nuclease-induced mutations in the GBSS gene. St226 refers to the experiment number, and the -# refers to the specific plant that was regenerated from experiment St226. Underlined nucleotides correspond to the TALE-nuclease binding site. The size of the deletion, the frequency of the sequenced alleles, and the SEQ ID NOS are shown to the right of the sequences.

FIG. 5 shows the genotype of plant St226-8, which contains TALE-nuclease-induced mutations in the GBSS gene. Underlined nucleotides correspond to the TALE-nuclease target site. The size of the deletion, the frequency of the sequenced alleles, and the SEQ ID NO are shown to the right of the sequences.

DETAILED DESCRIPTION

Figure 6:
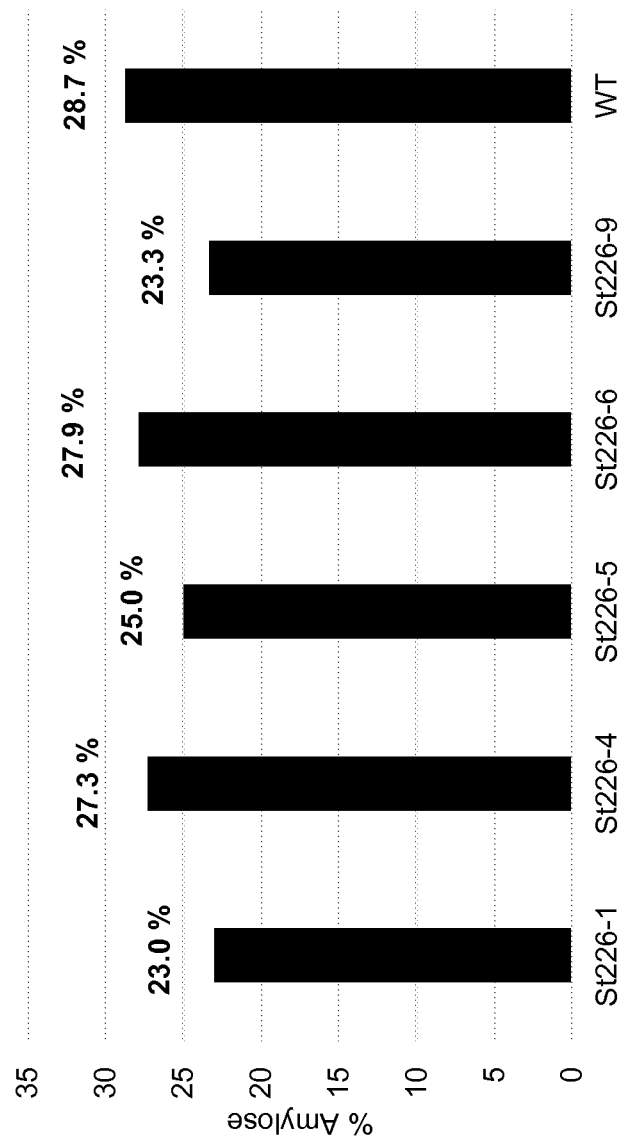
FIG. 6 is a graph plotting results from an amylose/amylopectin assay of tubers from plant lines St226-1, St226-2, St226-4, St226-5, St226-6, St226-9, and wild type (WT). The percent amylose for each line is shown above the corresponding bar.

The main component of potato tuber starch is a mixture of two glucose polymers, amylopectin and amylose. Amylopectin, which is the major component of starch, is a soluble branched glucose structure composed of chains of 20-25 $\alpha$-1,4 D-glucose residues with $\alpha$-1,6 branching linkages (Aiyer, *African J. Biotech.* 4(13):1525-1529, 2005). Amylose is an insoluble linear helical polymer with minimal branching that constitutes 20-30% of the starch in plant-storage organs (Denyer et al., *Biochem. J.* 340:183-191, 1999). The synthesis of amylose is due to the GBSS mechanism of transferring glucosyl residues from ADP-glucose to glucan substrates, such as malto-oligosaccharides, by $\alpha$-1,4 linkages (Aiyer, *African J. Biotech.* 4(13):1525-1529, 2005; and Zeeman et al., *Annu. Rev. Plant Biol.* 61:209-234, 2010). In many industrial applications, only the thickening amylopectin component is desired, but separating amylopectin from amylose typically is energy intensive and not economically viable.

This document provides potato plant varieties, particularly of the species *Solanum tuberosum*, that have reduced or even lack GBSS activity. Methods for generating such plant varieties, methods for using such plant varieties to produce industrial starch products, and industrial starch products produced from such plant varieties also are provided.

As used herein, the terms "plant" and "plant part" refer to cells, tissues, organs, seeds, and severed parts (e.g., roots, leaves, and flowers) that retain the distinguishing characteristics of the parent plant. "Seed" refers to any plant structure that is formed by continued differentiation of the ovule of the plant, following its normal maturation point at flower opening, irrespective of whether it is formed in the presence or absence of fertilization and irrespective of whether or not the seed structure is fertile or infertile.

The term "allele(s)" means any of one or more alternative forms of a gene at a particular locus. In a diploid (or amphidiploid) cell of an organism, alleles of a given gene are located at a specific location or locus on a chromosome, with one allele being present on each chromosome of the pair of homologous chromosomes. Similarly, in a tetraploid cell of an organism, one allele is present on each chromosome of the group of four homologous chromosomes. "Heterozygous" alleles are different alleles residing at a specific locus, positioned individually on corresponding homologous chromosomes. "Homozygous" alleles are identical alleles residing at a specific locus, positioned individually on corresponding homologous chromosomes in the cell.

"Wild type" as used herein refers to a typical form of a plant or a gene as it most commonly occurs in nature. A "wild type GBSS allele" is a naturally occurring GBSS allele (e.g., as found within naturally occurring *S. tuberosum* plants) that encodes a functional GBSS protein, while a "non-functional mutant GBSS allele" is a GBSS allele that does not encode a functional GBSS protein. Such a "non-functional mutant GBSS allele" can include one or more mutations in its nucleic acid sequence, where the mutation (s) result in a reduced or even no detectable amount of functional GBSS protein in the plant or plant cell in vivo.

"Mutagenesis" as used herein refers to processes in which mutations are introduced into a selected DNA sequence. Mutations induced by endonucleases generally are obtained by a double strand break, which results in insertion/deletion mutations ("indels") that can be detected by deep-sequencing analysis. Such mutations typically are deletions of several base pairs, and have the effect of inactivating the mutated allele. In the methods described herein, for example, mutagenesis occurs via double-stranded DNA breaks made by TALE-nucleases targeted to selected DNA sequences in a plant cell. Such mutagenesis results in "TALE-nuclease-induced mutations" (e.g., TALE-nuclease-induced knockouts) and reduced expression of the targeted gene. Following mutagenesis, plants can be regenerated from the treated cells using known techniques (e.g., planting seeds in accordance with conventional growing procedures, followed by self-pollination).

The term "expression" as used herein refers to the transcription of a particular nucleic acid sequence to produce sense or antisense RNA or mRNA, and/or the translation of an mRNA molecule to produce a polypeptide, with or without subsequent post-translational events.

"Reducing the expression" of a gene or polypeptide in a plant or a plant cell includes inhibiting, interrupting, knocking-out, or knocking-down the gene or polypeptide, such that transcription of the gene and/or translation of the encoded polypeptide is reduced as compared to a corresponding control plant, plant cell, or population of plants or plant cells in which expression of the gene or polypeptide is not inhibited, interrupted, knocked-out, or knocked-down. "Reduced expression" encompasses any decrease in expression level (e.g., a decrease of 10% or more, 20% or more, 30% or more, 40% or more, 50% or more, 60% or more, 70% or more, 80% or more, 90% or more, or even 100%) as compared to the corresponding control plant, plant cell, or population of plants or plant cells. In some embodiments, reducing expression by 50% or more may be particularly useful. Expression levels can be measured using methods such as, for example, reverse transcription-polymerase chain reaction (RT-PCR), Northern blotting, dot-blot hybridization, in situ hybridization, nuclear run-on and/or nuclear run-off, RNase protection, or immunological and enzymatic methods such as ELISA, radioimmunoassay, and western blotting.

The potato genome usually contains only one GBSS gene, but because cultivated potato is a tetraploid, multiple alleles of GBSS are present in each variety. The methods provided herein can be used to inactivate at least one (e.g., at least two, at least three, or all four) functional alleles of GBSS, thereby removing at least some full-length RNA transcripts and functional GBSS protein from potato cells, and in some cases completely removing all full-length RNA transcripts and functional GBSS protein.

A representative example of a naturally occurring *S. tuberosum* GBSS nucleotide sequence is shown in FIG. 2 (SEQ ID NO:4). In some embodiments, the *S. tuberosum* plants, cells, plant parts, seeds, and progeny thereof that are provided herein can have a mutation in each endogenous GBSS allele, such that expression of the gene is reduced or completely inhibited. Thus, in some cases, the plants, cells, plant parts, seeds, and progeny do not exhibit detectable levels of granule-bound starch synthase expressed from the GBSS gene.

The plants, plant cells, plant parts, seeds, and progeny provided herein can be generated using a rare-cutting endonuclease (e.g., a transcription activator-like effector nuclease (TALE-nuclease)) system to make a targeted knockout in one or more alleles of the GBSS gene. Thus, this document provides materials and methods for using rare-cutting endonucleases (e.g., TALE-nucleases) to generate potato plants and related products (e.g., seeds and plant parts) that are particularly suitable for providing reduced-amylose starch, due to targeted knockouts in the GBSS gene. Other sequence-specific nucleases also may be used to generate the desired plant material, including engineered homing endonucleases or zinc finger nucleases (ZFNs).

The term "rare-cutting endonuclease" as used herein refers to a natural or engineered protein having endonuclease activity directed to a nucleic acid sequence with a recognition sequence (target sequence) about 12-40 bp in length (e.g., 14-40, 15-36, or 16-32 bp in length; see, e.g., Baker, *Nature Methods* 9:23-26, 2012). Typical rare-cutting endonucleases cause cleavage inside their recognition site, leaving 4 nt staggered cuts with 3'OH or 5'OH overhangs. In some embodiments, a rare-cutting endonuclease can be a meganuclease, such as a wild type or variant homing endonuclease (e.g., a homing endonuclease belonging to the dodecapeptide family (LAGLIDADG; SEQ ID NO:18); see, WO 2004/067736). In some embodiments, a rare-cutting endonuclease can be a fusion protein that contains a DNA binding domain and a catalytic domain with cleavage activity. TALE-nucleases and ZFNs are examples of fusions of DNA binding domains with the catalytic domain of the endonuclease FokI. Customized TALE-nucleases are commercially available under the trade name TALEN™ (Cellectis, Paris, France).

Transcription activator-like (TAL) effectors are found in plant pathogenic bacteria in the genus *Xanthomonas*. These proteins play important roles in disease, or trigger defense, by binding host DNA and activating effector-specific host genes (see, e.g., Gu et al., *Nature* 435:1122-1125, 2005; Yang et al., *Proc. Natl. Acad. Sci. USA* 103:10503-10508, 2006; Kay et al. *Science* 318:648-651, 2007; Sugio et al., *Proc. Natl. Acad. Sci. USA* 104:10720-10725, 2007; and Römer et al. *Science* 318:645-648, 2007). Specificity depends on an effector-variable number of imperfect, typically 34 amino acid repeats (Schornack et al., *J. Plant Physiol.* 163:256-272, 2006; and WO 2011/072246). Polymorphisms are present primarily at repeat positions 12 and 13, which are referred to herein as the repeat variable-diresidue (RVD).

The RVDs of TAL effectors correspond to the nucleotides in their target sites in a direct, linear fashion, one RVD to one nucleotide, with some degeneracy and no apparent context dependence. This mechanism for protein-DNA recognition enables target site prediction for new target specific TAL effectors, as well as target site selection and engineering of new TAL effectors with binding specificity for the selected sites.

TAL effector DNA binding domains can be fused to other sequences, such as endonuclease sequences, resulting in chimeric endonucleases targeted to specific, selected DNA sequences, and leading to subsequent cutting of the DNA at or near the targeted sequences. Such cuts (double-stranded breaks) in DNA can induce mutations into the wild type DNA sequence via NHEJ or homologous recombination, for example. In some cases, TALE-nucleases can be used to facilitate site directed mutagenesis in complex genomes, knocking out or otherwise altering gene function with great precision and high efficiency. As described in the Examples below, TALE-nucleases targeted to the *S. tuberosum* GBSS gene can be used to mutagenize the endogenous gene, resulting in plants without detectable expression of GBSS. The fact that some endonucleases (e.g., FokI) function as dimers can be used to enhance the target specificity of the TALE-nuclease. For example, in some cases a pair of TALE-nuclease monomers targeted to different DNA sequences (e.g., the underlined target sequences shown in FIG. 1; SEQ ID NO:2 and 3) can be used. When the two TALE-nuclease recognition sites are in close proximity, as depicted in FIG. 1, the inactive monomers can come together to create a functional enzyme that cleaves the DNA. By requiring DNA binding to activate the nuclease, a highly site-specific restriction enzyme can be created.

In some embodiments, a mutated *Solanum* plant, plant part, or plant cell as provided herein can have its expression of GBSS reduced by about 50 percent or more (e.g., by 60 percent or more, 70 percent or more, 80 percent or more, or 90 percent or more) as compared to a control *Solanum* plant or to a population of control *Solanum* plants that lacks the mutation(s). The control *Solanum* plant can be, for example, a corresponding wild-type version of the *Solanum* plant in which the GBSS gene was mutated.

Further, the amylose level in a mutated *Solanum* plant as provide herein can be decreased by about 1 percent or more (e.g., 1 to 5%, 5 to 10%, 10 to 20%, 20 to 30%, 30 to 40%, 40 to 50%, 50 to 60%, 60 to 70%, 70 to 80%, 80 to 90%, or 90 to 100%) as compared to the control *Solanum* plant or population of *Solanum* plants. The term "reduced amylose" or "decreased amylose" refers to a decrease in amylose levels relative to amylopectin levels within potato tuber starch. For example, starch from tubers of a wild type potato plant contains an approximate amylose/amylopectin ratio of 25/75. Starch from tubers of a potato plant with reduced amylose can have amylose/amylopectin ratios lower than 25/75 (e.g., 20/80, 15/85, 10/90, 5/95, or 0/100). The amylose/amylopectin ratio can also be defined as a percentage. For example, an amylose/amylopectin ratio of 25/75, 20/80, 15/85, 10/90, 5/95, or 0/100 can also be represented as 25% amylose, 20% amylose, 15% amylose, 10% amylose, 5% amylose or 0% amylose, respectively. Thus, in some embodiments, a plant as provided herein can have 20-25%, 20-23%, or 23-25% amylose (e.g., when only one or two GBSS alleles are mutated). In some embodiments, such as when three or all four of the GBSS alleles are mutated, a plant as provided herein can have 15-20%, 10-15%, 5-10%, or 0-5% amylose. Methods for measuring amylose levels in plants are known in the art. See, e.g., Hovenkamp-Hermelink et al., *Potato Research* 31:241-246, 1988.

In some cases, a *Solanum* plant, plant part, or plant cell as provided herein can contain a GBSS nucleotide sequence with at least about 75 percent sequence identity to a representative GBSS nucleotide sequence. For example, a nucleotide sequence can have at least 75 percent, at least 80 percent, at least 85 percent, at least 90 percent, at least 91 percent, at least 92 percent, at least 93 percent, at least 94 percent, at least 95 percent, at least 96 percent, at least 97 percent, at least 98 percent, or at least 99 percent sequence identity to a representative, naturally occurring GBSS nucleotide sequence (e.g., SEQ ID NO:4).

In some cases, a mutation can be at a target sequence as set forth in a GBSS sequence as set forth herein (e.g., SEQ ID NO:1 or SEQ ID NO:4), or at a target sequence that is at least 95 percent (e.g., at least 96 percent, at least 97 percent, at least 98 percent, or at least 99 percent) identical to the sequence set forth in a GBSS sequence as set forth herein (e.g., SEQ ID NO:1 or SEQ ID NO:4).

The percent sequence identity between a particular nucleic acid or amino acid sequence and a sequence referenced by a particular sequence identification number is determined as follows. First, a nucleic acid or amino acid sequence is compared to the sequence set forth in a particular sequence identification number using the BLAST 2 Sequences (Bl2seq) program from the stand-alone version of BLASTZ containing BLASTN version 2.0.14 and BLASTP version 2.0.14. This stand-alone version of BLASTZ can be obtained online at fr.com/blast or at ncbi.nlm.nih.gov. Instructions explaining how to use the Bl2 seq program can be found in the readme file accompanying BLASTZ. Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -1; -r is set to 2; and all other options are left at their default setting. For example, the following command can be used to generate an output file containing a comparison between two sequences: C:\Bl2seq -i c:\seq1.txt -j c:\seq2.txt -p blastn -o c:\output.txt -q -1 -r 2. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq2.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence (e.g., SEQ ID NO:1), or by an articulated length (e.g., 100 consecutive nucleotides or amino acid residues from a sequence set forth in an identified sequence), followed by multiplying the resulting value by 100. For example, a nucleic acid sequence that has 200 matches when aligned with the sequence set forth in SEQ ID NO:1 is 83.3 percent identical to the sequence set forth in SEQ ID NO:1 (i.e., 200÷240×100=83.3). It is noted that the percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. It also is noted that the length value will always be an integer.

Methods for selecting endogenous target sequences and generating TALE-nucleases targeted to such sequences can be performed as described elsewhere. See, for example, PCT Publication No. WO 2011/072246, which is incorporated herein by reference in its entirety. In some embodiments, software that specifically identifies TALE-nuclease recognition sites, such as TALE-NT 2.0 (Doyle et al., *Nucleic Acids Res* 40:W117-122, 2012) can be used.

Methods for using rare-cutting endonucleases (e.g., TALE-nucleases) to generate potato plants, plant cells, or plant parts having mutations in endogenous genes include, for example, those described in the Examples herein. For example, one or more nucleic acids encoding TALE-nucleases targeted to selected GBSS sequences (e.g., the GBSS sequence shown in FIG. 1) can be transformed into plant cells (e.g., protoplasts), where they can be expressed. In some cases, one or more TALE-nuclease proteins can be introduced into plant cells (e.g., protoplasts). The cells, or a plant cell line or plant part generated from the cells, can subsequently be analyzed to determine whether mutations have been introduced at the target site(s), through nucleic acid-based assays or protein-based assays to detect expression levels as described above, for example, or using nucleic acid-based assays (e.g., PCR and DNA sequencing, or PCR followed by a T7E1 assay; Mussolino et al., *Nucleic Acids Res.* 39:9283-9293, 2011) to detect mutations at the genomic loci. In a T7E1 assay, genomic DNA can be isolated from pooled calli, and sequences flanking TALE-nuclease recognition sites for GBSS can be PCR-amplified. Amplification products then can be denatured and re-annealed. If the re-annealed fragments form a heteroduplex, T7 endonuclease I cuts at the site of mismatch. The digested products can be visualized by gel electrophoresis to quantify mutagenesis activity of the TALE-nuclease.

In some embodiments, a method as provided herein can include contacting a population of *Solanum* plant cells (e.g., protoplasts) having a functional GBSS allele with a rare-cutting endonuclease that is targeted to an endogenous GBSS sequence, selecting from the population a cell in which at least one (e.g., one, two, three, or four) GBSS alleles have been inactivated, and growing the selected cell into a *Solanum* plant. The plant may have reduced amylose levels, as compared to a control *Solanum* plant that does not contain the inactivated GBSS alleles. The rare-cutting endonuclease can be introduced into the population of cells via a nucleic acid (e.g., a vector or a mRNA) that encodes the rare-cutting endonuclease, or as a protein. In some cases, a method as provided herein can include a step of culturing a plant cell containing the inactivated GBSS allele(s) to generate one or more plant lines. In addition or alternatively, a method as provided herein can include a step of isolating genomic DNA containing at least a portion of the GBSS locus from the plant cells.

In some embodiments, methods for delivering sequence-specific nucleases to a *Solanum* plant can include *Agrobacterium*-mediated transformation of plant parts or plant cells (e.g., leaves, stems, petiole, internode explants, callus, or protoplasts) with T-DNA encoding the sequence-specific nucleases (see, for example, Beaujean et al., *J. Exp. Biol.* 49:1589-1595, 1998), biolistic transformation of plant parts or plant cells with one or more nucleic acids encoding the sequence-specific nucleases (see, for example, Craig et al., *Plant Cell Reports* 24:603-611, 2005), and/or cell-penetrating peptide-mediated transformation of plant parts or plant cells with purified sequence-specific nucleases or nucleic acids (RNA or DNA) encoding the sequence-specific nucleases (see, for example, Chen et al., *FEBS Lett.* 581:1891-1897, 2007).

In some embodiments, *Solanum* lines having mutations in one or more GBSS alleles can be generated by polyethylene glycol- (PEG-) mediated transformation. For example, protoplasts can be isolated from surface sterilized leaves, and transformed in the presence of PEG with plasmids encoding one or more sequence specific nucleases. Transformation efficiencies can be monitored by delivery of a detectable marker such as a YFP plasmid, which can be visualized using fluorescence microscopy or flow cytometry. After PEG-mediated transformation, protoplasts can be cultured using methods and media described elsewhere (see, e.g., Gamborg et al., in: *Plant Tissue Culture Methods and Applications in Agriculture*, Thorpe (Ed.), Academic Press, Inc., New York, N.Y., 1981, pp.115-153). After a suitable length of time in culture, protoplast-derived calli identified as mutants can be grown, transferred to shoot-inducing medium, and then (once roots form) transferred to soil and grown to maturity for tuber production (see, e.g., Haberlach et al., supra; and Gamborg et al., supra).

In some embodiments, delivery of one or more sequence-specific nucleases to a *Solanum* plant can be achieved through transient delivery or stable integration into the host genome. To transiently deliver sequence-specific nucleases, transformed potato plant parts or plant cells (using the above-described methods) can be placed on regeneration medium containing no selective agent, and potato plants can be regenerated. Regenerated plants then can be screened to identify those containing nuclease-induced mutations. To stably integrate the genome engineering reagents into the host genome, nucleic acids encoding the sequence-specific nucleases can be co-delivered with nucleic acid encoding a plant selectable marker (e.g., kanamycin [nptII], hygromycin [hpt], methotrexate [dhfr], phosphinothricin [bar], or phleomycin [ble]). The selectable marker can be harbored on the same vector as the sequence-specific nuclease(s), or can be delivered as a separate vector. After transformation, potato plant parts or plant cells can be placed on regeneration medium containing the appropriate selectable agent, and transgenic potato plants can be regenerated.

In some embodiments, a nuclease can be co-delivered to a plant cell with a plasmid encoding one or more exonuclease proteins to increase sequence specific nuclease induced mutagenesis efficiency. Such exonucleases include, without limitation, members of the TREX (Therapeutic red cell exchange exonucleases) family of exonucleases, such as TREX2 (Shevelev et al., *Scientific World Journal* 2:275-281, 2002). Co-delivery of an exonuclease such as TREX with one or more rare-cutting endonucleases (e.g., TALE-nucleases) may increase the frequency of NHEJ events, as compared with the frequency of NHEJ events after delivery of the rare-cutting endonuclease(s) alone. It is to be noted that other exonucleases also can be used in the methods provided herein.

Another genome engineering tool that can be used in the methods provided herein is based on the RNA-guided Cas9 nuclease from the type II prokaryotic CRISPR (Clustered Regularly Interspaced Short palindromic Repeats) adaptive immune system (see, e.g., Belahj et al., *Plant Methods* 9:39, 2013). This system allows for cleavage of DNA sequences that are flanked by a short sequence motif, referred as proto-spacer adjacent motif (PAM). Cleavage is achieved by engineering a specific crRNA that is complementary to the target sequence. The crRNA associates into a living cell with a heterologously expressed Cas9 endonuclease from *Streptococcus pyogenes*. In the crRNA/Cas9 complex, a dual tracrRNA:crRNA structure acts as a guide RNA that directs the Cas9 endonuclease to the cognate target sequence. Since several PAM motifs are present in the nucleotide sequence of the GBSS gene, crRNA specific to GBSS gene can be designed to introduce mutations or to inactivate one or more GBSS alleles within *Solanum* plant cells into which the Cas9 endonuclease and the crRNA are transfected and then expressed. In some embodiments, therefore, this approach can be used to obtain GBSS mutant plants as described herein.

In some embodiments, the plants provided herein can contain further mutations introduced into other *Solanum* genes. Such mutations can, for example:

provide acrylamide reduction by modifying the expression of genes involved in asparagine synthesis;

prevent black spot bruise by reducing polyphenol oxidase-5 expression;

prevent Potato Virus Y by reducing eIF4E gene expression;

prevent late blight; and/or improve nematode, herbicide, or insect resistance.

Thus, the methods provided herein can be used to obtain gene stacking in a *Solanum* trait.

This document also provides methods for producing starch products using potato plant varieties with reduced amylose, as well as industrial starch products made by such methods. These products include, without limitation, starches useful in the paper, textile, adhesive, and packing industries. Such starch products can be produced using various procedures and types of equipment, although all follow a similar process. For example, potatoes can be dropped into water flumes that clean the potatoes of stones and dirt. After further cleaning in a washer, the potatoes can be moved to a grinder or crusher to liberate the starch from the potato cells. The resulting slurry can be passed through a screen or rotary sieve to separate the fiber and potato skins, and the starch solution can then be further purified to remove soluble and insoluble impurities by alternate cycles of filtration and redispersion in water. The purified starch then can be dewatered, dried, and collected. See, for example, Robson, "U.S. Enviromental Protection Agency. Starch Manufacturing: A Profile," North Carolina: Center for Economics Research, March 1994 (RTI Project Number: 35U-5681-71 DR).

The invention will be further described in the following examples, which do not limit the scope of the invention described in the claims.

EXAMPLES

Example 1—Engineering Sequence-Specific Nucleases to Mutagenize the GBSS Gene

To completely inactivate or knock-out the alleles of the GBSS gene in *S. tuberosum*, sequence-specific nucleases were designed to target the protein coding region in the first exon. In particular, a pair of TALE-nucleases (designated as GBSS_T1) was designed to target the GBSS gene family within the first 150 bp of the coding sequence, using software that specifically identifies TALE-nuclease recognition sites. The TALE-nuclease recognition sites for the GBSS genes are underlined in FIG. 1 and are listed in Table 1 (SEQ ID NOS:2 and 3). TALE-nucleases were synthesized using methods similar to those described elsewhere (Cermak et al., *Nucleic Acids Res.* 39:e82, 2011; Reyon et al., *Nat. Biotechnol.* 30:460-465, 2012; and Zhang et al., *Nat. Biotechnol.* 29:149-153, 2011).

Example 2—Activity of GBSS TALE-Nucleases at their Endogenous Target Sites in *S. tuberosum*

GBSS_T1 activity at endogenous target sites in *S. tuberosum* was measured by expressing the TALE-nucleases in protoplasts and subsequently surveying the target sites for mutations introduced by NHEJ. Methods for protoplast preparation were performed as described elsewhere (Shepard, in: *Genetic Improvement of Crops/Emergent Techniques*, Rubenstein, Gengenbach, Philips, and Green (Eds.), Univ. of Minnesota Press, Minneapolis, Minn., 1980, pp.185-219); and Shepard and Totten, *Plant Physiol.* 60:313-316, 1977). Briefly, *S. tuberosum* mini tubers were planted in moistened vermiculite and grown under low light conditions for 3-5 weeks. Young, fully expanded leaves were collected and surface sterilized, and protoplasts were isolated.

TALE-nuclease-encoding plasmids, together with a yellow fluorescent protein-(YEP-) encoding plasmid, were introduced into *S. tuberosum* protoplasts by polyethylene glycol- (PEG-) mediated transformation (Yoo et al., *Nature Protocols* 2:1565-1572, 2007). In some experiments, a plasmid encoding a TREX2 exonuclease was co-delivered with the TALE-nuclease-encoding plasmid. Twenty-four hours after treatment, transformation efficiency was measured using a fluorescent microscope to monitor YFP fluorescence in an aliquot of the transformed protoplasts. The remainder of the transformed protoplasts was harvested, and genomic DNA was prepared using a hexadecyltrimethylammonium bromide- (CTAB-) based method. Using genomic DNA prepared from the protoplasts as a template, a 491-bp fragment encompassing the TALE-nuclease recognition site was amplified by PCR. Allele types were analyzed by individual clonal direct sequencing and 454 pyro-sequencing. Sequencing reads with indel mutations in the spacer region were considered to be derived from imprecise repair of a cleaved TALE-nuclease recognition site by NHEJ. Mutagenesis frequency was calculated as the number of sequencing reads with NHEJ mutations out of the total sequencing reads.

The activity of the GBSS TALE-nuclease pair, with or without TREX2, is summarized in Table 2. The TALE-nucleases induced NHEJ mutations in GBSS_T1 in 11% to 23% of the sequencing reads. Examples of TALE-nuclease-induced mutations in GBSS_T1 are shown in FIG. 3.

Example 3—Regeneration of *S. tuberosum* Lines with TALE-nuclease-induced GBSS Mutations Transgenic potato plant lines encoding the GBSS_T1 TALE-nuclease pair, were generated by *Agrobacterium*-mediated transformation of internodes. Briefly, the coding sequence for the GBSS_T1 TALE-nuclease pair was cloned into T-DNA. Methods for transforming potato using *Agrobacterium*-mediated transformation of internodes were followed as previously described (Beaujean et al., supra).

Example 4—Verification of *S. tuberosum* Lines with TALE-nuclease-induced GBSS Mutations Transgenic potato plants encoding the GBSS_T1 TALE-nuclease pair were assessed for mutations at the GBSS_T01 target site. To this end, genomic DNA was isolated from leaf tissue using a CTAB-based method (Murray and Thompson, *Nucl. Acids Res.* 8:4321-4326, 1980). The isolated genomic DNA was then used as a template in a PCR reaction with primers designed to amplify the TALE-nuclease target site. The resulting amplicons were cloned and sequenced. Seven plants were identified that contained mutations in at least one GBSS allele. A list of the GBSS-mutant plant genotypes are shown in (FIGS. 4A, 4B, and 5).

Example 5—Determining Whether Mutant *S. tuberosum* Lines have Desired Phenotypes GBSS transcript quantification is determined using quantitative real-time PCR with cDNA generated from mutant and control tuber mRNA extracts (Bhaskar et al., *Plant Physiol.* 154(2):939-948, 2010). The level and any reduction of GBSS expression is quantified using a comparative cycle threshold method (Livak and Schmittgen, *Method. Methods* 25:402-408, 2001). Amylose levels are assessed using methods and media described elsewhere (Hovenkamp-Hermelink et al., supra), and/or using the amylose/amylopectin assay kit (K-AMYL; Megazyme, Ireland).

Tubers from candidate plants harboring mutations in the GBSS alleles were assessed for amylose levels using the K-AMYL amylose/amylopectin assay kit (Megazyme). Briefly, approximately 1 gram of potato tuber was ground to a paste using a mortar and pestle. About 50 mg of material was collected in a glass test tube and 1 mL of DMSO was added. The samples were vortexed and boiled for about 15 minutes. The samples were then incubated at room temperature for 5 minutes. Starch was precipitated from the samples by adding 6 mL of 95% ethanol. Samples were centrifuged at 2,000 g for 5 minutes and supernatant was removed. After allowing the ethanol to evaporate, the starch was dissolved in 2 mL of DMSO and the tubes were placed in a boiling water bath for 15 minutes. Following boiling, the samples were diluted in a concanavalin A (ConA) buffer to a total volume of 25 mL. The amylose and amylopectin content of this "total starch" solution was determined by adding 0.1 mL of an amyloglucosidase/alpha-amylase solution to 0.5 mL of the total starch solution and incubating the resulting solution for 10 minutes at 40° C. Next, 4 mL of a GOPOD reagent containing glucose oxidase plus peroxidase and 4-aminoantipyrine was added to the total starch solution. The total starch content was measured colorimetrically using a plate reader at 510 nm.

To determine the fraction of amylose within the total starch, 0.50 mL of the solution containing ConA was added to 1 mL of the total starch solution, which was then incubated at room temperature for 1 hour. The solution was boiled for 5 minutes to inactivate ConA, and the resulting sample was incubated at 40° C. for 5 minutes, and then 0.1 mL of the amyloglucosidase/alpha-amylase solution was added. The solution was incubated at 40° C. for 30 minutes. The sample was centrifuged at 2,000 g for 5 minutes and the supernatant was collected. To 1 mL of supernatant, 4 mL of the GOPOD reagent was added, and the sample was incubated at 40° C. for 20 minutes. The amylose fraction was measured colorimetrically using a plate reader at 510 nm. The percentage of amylose was determined using the following equation: (510 nm absorbance of the amylose supernatant)/(510 nm absorbance of the total starch supernatant)× 6.15/9.2×100/1.

Figure 7:
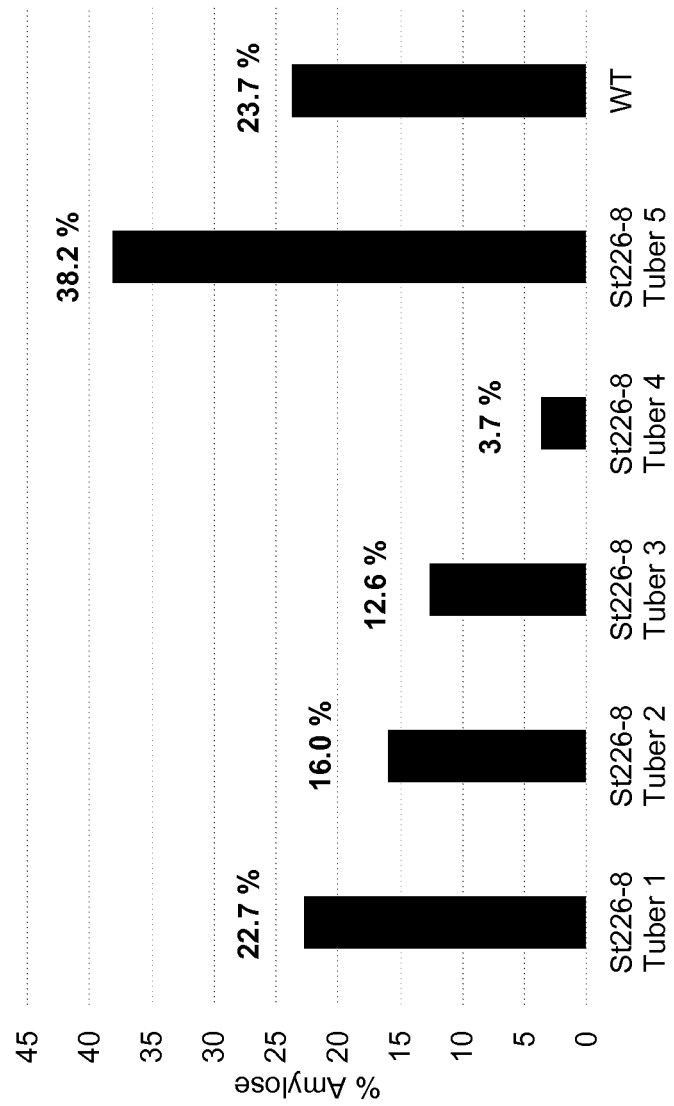
FIG. 7 is a graph plotting results from an amylose/amylopectin assay of tubers from plant lines St226-8 and WT. Five different tubers, labeled Tuber 1-Tuber 5, were sampled from line St226-8. The percent amylose is for each line is shown above the corresponding bar.

The results of the amylose/amylopectin kit are shown in FIGS. 6 and 7. Tuber starch from plant lines St226-1, St226-2, St226-4, St226-5, St226-6 and St226-9 all contained amylose/amylopectin ratios similar to the tuber starch from wild type plants. Specifically, St226-1 contained 23.0% amylose and 77% amylopectin; St226-4 contained 27.3% amylose and 72.7% amylopectin; St226-5 contained 25.0% amylose and 75% amylopectin; St226-6 contained 27.9% amylose and 72.1% amylopectin; St226-9 contained 23.3% amylose and 76.7% amylopectin; wild type potato plants contained 28.7% amylose and 71.3% amylopectin. The genotype data presented in FIG. 4, along with the phenotype data presented in FIG. 6, suggest that potato plants containing one or more wild type GBSS alleles can produce tuber starch that has an amylose/amylopectin ratio similar to tuber starch from an unmodified, wild type plant.

While tubers from plant lines St226-1, St226-2, St226-4, St226-5, St226-6 and St226-9 all contained amylose/amylopectin ratios similar to tubers from wild type plants, plant line St226-8 produced specific tubers that contained substantially less amylose than tubers from WT plants (FIG. 7). Specifically, St226-8 Tuber 1 contained 22.7% amylose and 77.3% amylopectin; St226-8 Tuber 2 contained 16.0% amylose and 84.0% amylopectin; St226-8 Tuber 3 contained 12.6% amylose and 87.4% amylopectin; St226-8 Tuber 4 contained 3.7% amylose and 96.3% amylopectin; St226-8 Tuber 5 contained 22.7% amylose and 77.3% amylopectin; wild type potato tubers contained 23.7% amylose and 76.3% amylopectin. These results indicate that TALE-nuclease-induced mutations within the GBSS gene can result in potato tubers with reduced amylose, as compared to potato tubers from unmodified plants. Further, these results indicate that at least three mutant GBSS alleles are necessary to obtain potato tubers with reduced amylose, as compared to potato tubers from unmodified plants.

TABLE 1

TALE-nuclease target sequences in GBSS_T1

| Target Sequence Left | SEQ ID NO: | Target Sequence Right | SEQ ID NO: |
|---|---|---|---|
| TCTGACTCACAATGGTT | 2 | AGCTTGATGGGCTCCAA | 3 |

TABLE 2

Sequencing Data for GBSS TALE-nuclease

| Nucleases tested | Location of target site | NHEJ mutagenesis frequency |
|---|---|---|
| GBSS_T1 | GBSS_T1 | 11% |
| GBSS_T1 + TREX2 | GBSS_T1 | 23% |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for making a *Solanum* plant, comprising:
    (a) contacting a population of *Solanum* plant cells comprising a functional GBSS allele with a rare-cutting endonuclease targeted to an endogenous GBSS sequence, wherein said rare-cutting endonuclease is a TALE-nuclease, and wherein said TALE-nuclease binds to a sequence as set forth in SEQ ID NO:2 or SEQ ID NO:3,
    (b) selecting, from said population, a cell in which at least three GBSS alleles have been inactivated, wherein each of said at least three GBSS alleles comprises a deletion of more than one nucleotide base pair, and
    (c) growing said selected plant cell into a *Solanum* plant, wherein said *Solanum* plant has reduced levels of amylose as compared to a control *Solanum* plant in which said at least three GBSS alleles have not been inactivated.

2. The method of claim 1, wherein said *Solanum* plant cells are protoplasts.

3. The method of claim 2, comprising transforming said protoplasts with a nucleic acid encoding said rare-cutting endonuclease.

4. The method of claim 3, wherein said nucleic acid is an mRNA.

5. The method of claim 3, wherein said nucleic acid is contained within a vector.

6. The method of claim 2, comprising introducing into said protoplasts a rare-cutting endonuclease protein.

7. The method of claim 2, further comprising culturing said protoplasts to generate plant lines.

8. The method of claim 2, comprising isolating genomic DNA comprising at least a portion of the GBSS locus from said protoplasts.

9. The method of claim 1, wherein said *Solanum* plant cells are *S. tuberosum* plant cells.

* * * * *